United States Patent
Koizumi et al.

(10) Patent No.: US 10,213,239 B2
(45) Date of Patent: Feb. 26, 2019

(54) POROUS PLATE FOR MEDICAL USE AND MANUFACTURING METHOD OF POROUS PLATE FOR MEDICAL USE

(71) Applicant: FUKUSHIMA MEDICAL UNIVERSITY, Fukushima-shi, Fukushima (JP)

(72) Inventors: Toshirou Koizumi, Fujimi (JP); Hiroshi Hasegawa, Fukushima (JP); Hiroshi Ishihata, Sendai (JP); Naoki Miki, Saitama (JP)

(73) Assignee: FUKUSHIMA MEDICAL UNIVERSITY, Fukushima-Shi (JP)

(*) Notice: Subject to any disclaimer, the term of this patent is extended or adjusted under 35 U.S.C. 154(b) by 72 days.

(21) Appl. No.: 14/910,826

(22) PCT Filed: Sep. 1, 2014

(86) PCT No.: PCT/JP2014/072877
§ 371 (c)(1),
(2) Date: Feb. 8, 2016

(87) PCT Pub. No.: WO2015/030228
PCT Pub. Date: Mar. 5, 2015

(65) Prior Publication Data
US 2016/0183990 A1    Jun. 30, 2016

(30) Foreign Application Priority Data

Sep. 2, 2013 (JP) ................................ 2013-181662

(51) Int. Cl.
*A61F 2/02* (2006.01)
*A61B 17/80* (2006.01)
(Continued)

(52) U.S. Cl.
CPC ...... *A61B 17/8085* (2013.01); *A61B 17/8071* (2013.01); *A61C 8/0006* (2013.01);
(Continued)

(58) Field of Classification Search
CPC .................... A61B 17/8085; A61F 2/2846
See application file for complete search history.

(56) References Cited

U.S. PATENT DOCUMENTS 5,380,328 A * 1/1995 Morgan ............. A61B 17/8071
606/70
5,919,234 A   7/1999 Lemperle et al.
(Continued)

FOREIGN PATENT DOCUMENTS

JP    H06-319794 A    11/1994
JP    2002-510530 A    4/2002
(Continued)

OTHER PUBLICATIONS

Tokarev V N et al: "Suppression of Melt Flows in Laser Ablation: Application to Clean Laser Processing", Journal of Physics D: Applied Physics, Institute of Physics Publishing Ltd, GB, vol. 32, No. 13, Jun. 7, 1999, pp. 1526-1538.
(Continued)

*Primary Examiner* — Brian Dukert
(74) *Attorney, Agent, or Firm* — K&L Gates LLP

(57) ABSTRACT

To provide a porous plate for medical use which can suppress bending along a row direction and, even if a local crack occurs, can inhibit the crack from growing and leading to a fracture. One aspect of the present invention is a porous plate for medical use which is a thin-plate substrate provided with a pore perforation section having a plurality of pores perforated therein and a frame section surrounding the pore perforation section. In this porous plate, the pore perforation section has crosspieces which extend lengthwise and crosswise in continuity with the frame section and partition the pore perforation section into a plurality of parts, and a plurality of pore perforation cells each surrounded by the crosspieces. The pores perforated in the pore perforation cells have a pore diameter calculated as an equivalent circular pore diameter of 1 to 50 μm, and the center-to-center distance between the adjacent pores is 2 to 200 μm.

16 Claims, 16 Drawing Sheets

(51) Int. Cl.
    *C12M 1/12*     (2006.01)
    *A61C 8/02*     (2006.01)
    *B23K 26/38*     (2014.01)
    *A61F 2/28*     (2006.01)
    *A61B 17/00*     (2006.01)

(52) U.S. Cl.
    CPC .......... *A61F 2/2803* (2013.01); *A61F 2/2846* (2013.01); *B23K 26/38* (2013.01); *C12M 25/02* (2013.01); *A61B 2017/00526* (2013.01)

(56) References Cited

U.S. PATENT DOCUMENTS

| | | |
|---|---|---|
| 6,391,059 B1 | 5/2002 | Lemperle et al. |
| 2001/0012607 A1 | 8/2001 | Robinson |

FOREIGN PATENT DOCUMENTS

| | | |
|---|---|---|
| JP | 2002-325830 A | 11/2002 |
| JP | 2009-061109 A | 3/2009 |
| JP | 2011-142831 A | 7/2011 |
| JP | 2011-212209 A | 10/2011 |
| WO | 1999/051171 A1 | 10/1999 |

OTHER PUBLICATIONS

Extended European Search Report issued in the corresponding European application No. 14840369.4 dated Feb. 27, 2017.

\* cited by examiner

*Fig.6*
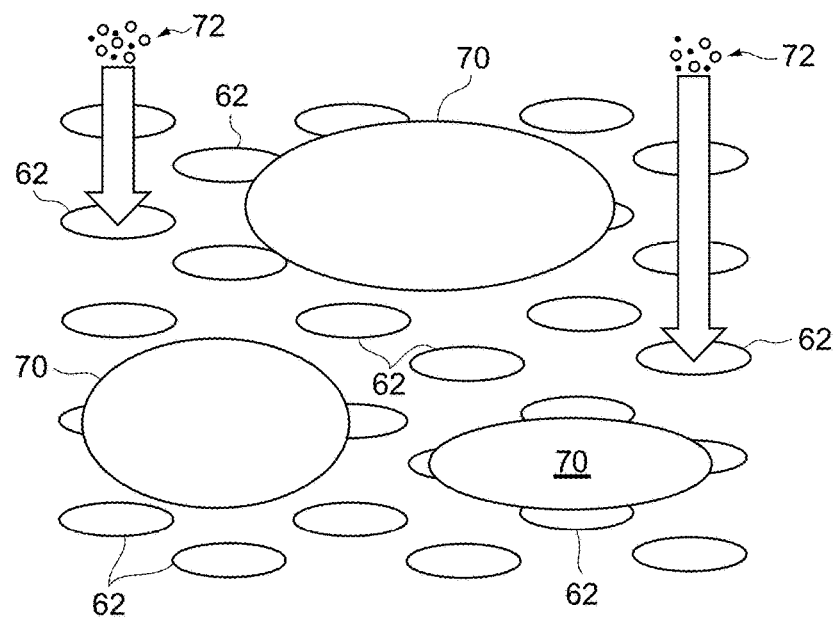
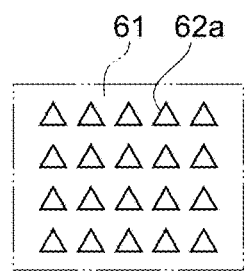
*Fig.7A*
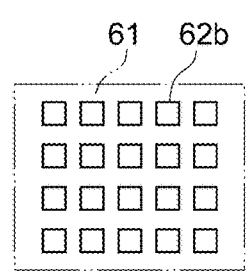
*Fig.7B*
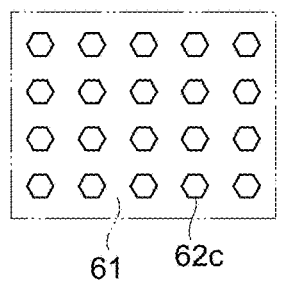
*Fig.7C*
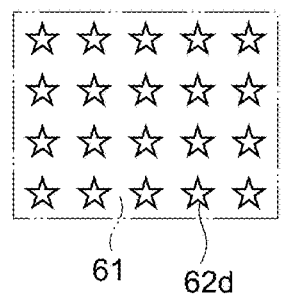
*Fig.7D*

| | Wave length | Pulse width | Heat affected zone(HAZ) |
|---|---|---|---|
| Example 1 | 1028 nm | 300 fsec | ≪1 μm |
| Example 2 | 532 nm | 500 psec | ~1 μm |
| Example 3 | 1060 nm | 5 nsec | ~2 μm |
| Comparative example 1 | 532 nm | 40 nsec | ~6 μm |

POROUS PLATE FOR MEDICAL USE AND MANUFACTURING METHOD OF POROUS PLATE FOR MEDICAL USE

TECHNICAL FIELD

The present invention relates to a porous plate for medical use which is used as a medical device in the field of medical treatment, such as tissue regeneration, and to a manufacturing method of a porous plate for medical use.

BACKGROUND ART

When tissue is damaged by injury, disease, etc., the morphology and function of the tissue can be restored by autonomous tissue reconstruction if that damage is of a minor extent. However, if the extent of the damage exceeds a certain limit, restoration of the original morphology and function by autonomous tissue reconstruction becomes difficult, and the tissue is left with sequelae which are changed in morphology and function. For example, while a tooth in a healthy state is held stably with its root supported by the surrounding alveolar bone, once the tooth is affected with periodontal disease, the alveolar bone is destroyed by an inflammatory reaction, and the lost part is replaced by granulation tissue.

One of the means for restoring bone tissue lost by disease etc. is the guided tissue regeneration (GTR) technique, and today this technique is commonly practiced in clinical dentistry. In the GTR technique, an isolation membrane is disposed between a tooth root and gingival soft tissue in the vicinity of the alveolar bone, which is destroyed and resorbed by being affected with periodontitis, to thereby release a space for regeneration of the alveolar bone and guide the regeneration from the remaining bone tissue.

The isolation membrane used in the GTR technique is required to have the functions of: maintaining a regeneration space by separating the gingival soft tissue and a regeneration site of the alveolar bone for a predetermined period of time according to the growth of the bone tissue; blocking entry of tissue from the gingival soft tissue to the regeneration site; and allowing permeation of nutrients, bioactive substances, etc. from the gingival soft tissue, which is rich in blood flow, to the regeneration site of the alveolar bone. In other words, an important function required of the isolation membrane is the filter effect of blocking passage of cells (serving as a barrier against cells) while allowing permeation of nutrients and bioactive substances. Thus, such an isolation membrane used for tissue regeneration medicine is called a barrier membrane.

Conventionally, barrier membranes made of a polymer material, such as polytetrafluoroethylene (PTFE), polylactide, or polyurethane, are used. A porous barrier membrane formed by sintering PTFE powder has also been put into practical use. In addition, other barrier membranes, such as a barrier membrane of polylactide formed into a non-woven fabric, and a barrier membrane of a multilayer filter composed of a spongy matrix layer made of collagen and a comparatively impermeable barrier layer, have been proposed (e.g., see Patent Literature 1, Patent Literature 2, and Patent Literature 3).

There have been two major problems pointed out with these conventional barrier membranes. The first problem is the thickness of the barrier membrane. Since the barrier membrane is implanted under the gingiva, it is required to have the physical strength to retain the membrane shape under the tissue pressure of the gingival soft tissue and maintain the regeneration space. In the case of the conventional barrier membranes made of a polymer material, the membrane thickness to meet this required physical strength is roughly 200 to 400 µm. As this thickness is equivalent to several tens of cells, implanting a barrier membrane of such a thickness under the gingiva may narrow the space for regeneration of the periodontal tissue. The second problem is the growth of bacteria inside the barrier membrane. To realize the filter function, barrier membranes made of a polymer material are in the form of a porous sintered body or fibers, and the matrix has an abundance of intricate small cavities. While cells having an approximate size of 10 µm in diameter do not enter the small cavities, bacteria not larger than one tenth of that size can easily enter the small cavities. Thus, once oral bacteria enter a part where the barrier membrane is implanted, the bacteria may grow inside the cavities, of which the number is said to be as huge as several hundred million per square centimeter, and may cause a local infection.

Recently, barrier membranes made of thin metal plate have been proposed. For example, Patent Literature 4 proposes a porous plate which is a thin metal plate having a large number of pores perforated therein by precision pressing using a micro-perforation punching die. Patent Literature 5 proposes a support for guided bone regeneration which is a thin metal plate having a large number of pores perforated therein by chemical etching processing using a photolithographic technique.

CITATION LIST

Patent Literature

Patent Literature 1: Japanese Patent Laid-Open No. 6-319794
Patent Literature 2: Japanese Patent Laid-Open No. 2002-325830
Patent Literature 3: Japanese Patent Laid-Open No. 2009-61109
Patent Literature 4: Japanese Patent Laid-Open No. 2011-142831
Patent Literature 5: Japanese Patent Laid-Open No. 2011-212209

SUMMARY OF INVENTION

Technical Problem

The porous plates intended for regeneration treatment as disclosed in Patent Literatures 4 and 5 have been expected to be potent means for solving the problems with the conventional barrier membranes made of a polymer material. However, these porous plates are faced with the following problems.

The first problem is local bends and development of cracks which occur as the plate is deformed. To use the porous plate as an isolation membrane, the part where a large number of pores are perforated is cut out with scissors etc. to match a treatment region, shaped so as to conform to the morphology of the affected area or the operative area where the plate is to be installed, and then fixed on the alveolar bone or the jawbone with pins etc. or fixed on the crown or the root of the tooth with a suture, wire, or the like. During the shaping, the porous plate is repeatedly and complicatedly deformed by an operator so as to obtain a suitable shape. The porous plate has a structure in which small pores are arrayed in high density in the thin plate. Since the array of the pores can be regarded as a collection of rows of perforation, the porous plate bends easily in the row direction, and when a local crack occurs, the crack is enlarged by a relatively small force, which may eventually lead to plate fracture.

The second problem is feasibility or productivity. To realize a function equivalent to that of the conventional barrier membrane made of a polymer material with a porous plate made of a metal material, it is necessary to perforate a large number of pores having a diameter of at least approximately 50 µm at a center-to-center distance of approximately 60 to 200 µm. It is extremely difficult to perforate such small-diameter and high-density pores in a thin metal plate by punching. In addition, when pores are perforated in high density in a thin metal plate by plastic working, generation of residual stress results in significant post-processing deformation. Thus, it seems difficult to produce a porous plate for medical applications, for which stable physical properties are required, stably at a realistic production cost. These problems attributable to plastic working do not arise in chemical etching processing using a photolithographic technique. However, this processing method has problems in that uniform perforating is difficult when the plate thickness of a metal material is large, and that the work is complicated and the production efficiency is low due to numerous steps involved.

The problems attributable to plastic working do not arise in perforating by laser, either, as it is performed in a non-contact manner. However, laser processing performed on metal materials is basically thermal processing. Titanium, which is a typical example of the substrate used in tissue regeneration, is a metal extremely reactive with other elements at high temperatures, and titanium melted by thermal processing instantly combines with oxygen and is vitrified. Since vitrified titanium has lost its flexibility, brittle fracture is likely to occur if the vitrified region increases. Thus, it has also been considered to be difficult to manufacture a porous plate for medical use by laser processing (see Patent Literature 4).

The present invention has been devised to solve the problems peculiar to a porous plate in which small pores are perforated in high density, and an object of the invention is to provide a porous plate for medical use which can suppress bending along a row direction and, even if a local crack occurs, can inhibit the crack from growing and leading to a fracture. Another object of the present invention is to provide a production method of a porous plate which can stably produce such a porous plate.

Solution to Problem

A first aspect exemplifying the present invention is a porous plate for medical use which is a thin-plate substrate provided with a pore perforation section having a plurality of pores perforated therein and a frame section surrounding the pore perforation section. In this porous plate, the pore perforation section has crosspieces which extend lengthwise and crosswise in continuity with the frame section and partition the pore perforation section into a plurality of parts, and a plurality of pore perforation cells each surrounded by the crosspieces. The pores perforated in the pore perforation cells have a pore diameter calculated as an equivalent circular pore diameter of 1 to 50 µm, and the center-to-center distance between adjacent pores is 2 to 200 µm. Here, in this specification, a pore diameter calculated as an equivalent circular pore diameter refers to the diameter of a circle when the pores have a circular shape, and refers to the diameter of the inscribed circle of a triangle, quadrangle, polygon with more than four sides, star shape, etc. when the pores have such a shape.

The substrate can be a biocompatible metal material having a plate thickness of 2 to 100 µm. The size of the pore perforation cell surrounded by the crosspieces can be such that the inscribed circle of the cell is 0.5 to 5 mm in diameter. The width of the crosspieces can be 0.1 to 0.5 mm. In addition to the pores, second pores having a pore diameter calculated as an equivalent circular pore diameter of 80 to 220 µm can be perforated in the pore perforation cells dispersedly at a center-to-center distance of 2 to 4 mm.

The pore perforation cells surrounded by the crosspieces can each have a regular polygonal shape, and the pore perforation cells can be formed in a uniform distribution in the pore perforation section. In this specification, a polygon refers to a plane figure surrounded by three or more sides, and a regular polygon refers to a polygon with sides of all the same length. Alternatively, the pore perforation cells surrounded by the crosspieces can each have a hexagonal shape with parallel opposite sides, and the pore perforation cells can be formed in a honeycomb distribution in the pore perforation section.

Second and third aspects exemplifying the present invention are manufacturing methods of a porous plate for medical use. Before describing these aspects of the present invention in terms of their configurations, the relation between the pulse width of a laser beam radiated to a substrate and a heat diffusion length of the substrate will be described with reference to FIG. 1. FIG. 1 is a graph showing the relation between the pulse width of a laser beam radiated to the substrate and the diffusion length of heat generated in the substrate as a result of irradiation with the laser beam (heat diffusion length), and the graph is plotted for various materials used for medical purpose on the basis of calculation in accordance with the theory of heat diffusion.

In the heat diffusion theory, a heat diffusion length δ is expressed by the following formula (Laser Ablation and Its Applications, The Institute of Electrical Engineers of Japan, Nov. 25, 1999, Corona Publishing):

$$\delta = (12\kappa\tau)^{1/2} \quad (1)$$

Here, κ is the heat diffusion coefficient of the substrate, and τ is the pulse width of the laser beam radiated to the substrate.

It can be understood from the above formula (1) that the larger the pulse width T of the laser beam radiated to the substrate, the larger the heat diffusion length δ, and the larger the heat diffusion coefficient κ of the substrate, the larger the heat diffusion length δ. The formula (1) also means that, if the type of material (i.e., the heat diffusion coefficient κ) of the substrate used as a porous plate is identified, the pulse width τ for achieving a desired value of the heat diffusion length δ of heat generated by laser beam irradiation can be obtained. The heat diffusion length represents an elementary process of propagation of heat generated by irradiation with a single pulsed laser beam. Since perforating by laser pulses is performed by radiating a large number of short pulses to the same position, the heat diffusion length is an accumulation of elementary processes of heat diffusion. As a result of this accumulation of elementary processes, a temperature rise and change in quality associated therewith of a workpiece can be estimated. For this reason, the heat diffusion length serves as a reference for thermal effects of pulsed laser processing.

In FIG. 1, titanium (Ti), stainless steel (SUS), silver (Ag), magnesium (Mg), and alumina ceramics are selected as examples from various materials used for medical purpose, and the results of calculation of the relation between the pulse width τ and the heat diffusion length δ when these materials are irradiated with a laser beam are plotted. Here, the value used as the heat diffusion coefficient κ is 300K which is an ambient temperature. FIG. 1 shows that, when the substrate is alumina ceramics, for example, the pulse width of the laser beam can be set to about 60 nsec (nanoseconds) to achieve a heat diffusion length of 3 μm, and the pulse width of the laser beam needs to be set to about 30 nsec or less to suppress the heat diffusion length to 2 μm or less.

The second aspect exemplifying the present invention is a manufacturing method of a porous plate for medical use involving irradiating a thin-plate substrate with a laser beam and perforating a plurality of pores in a pore perforation section surrounded by a frame section. In the manufacturing method of this aspect, the pore perforation section, except for crosspieces which extend lengthwise and crosswise in continuity with the frame section and partition the pore perforation section into a plurality of parts, is irradiated with a laser beam having a pulse width determined on the basis of a heat diffusion length in the substrate; pores are perforated which have a pore diameter calculated as an equivalent circular pore diameter of 1 to 50 μm and of which the center-to-center distance between adjacent pores is 2 to 200 μm; and a plurality of pore perforation cells, each of which is surrounded by the crosspieces and has a plurality of the pores perforated therein, are formed in the pore perforation section.

The substrate can be a biocompatible metal material having a plate thickness of 2 to 100 μm. The heat diffusion length can be 1 μm or less. The pulse width can be 10 nsec or less.

The third aspect exemplifying the present invention is a manufacturing method of a porous plate for medical use involving irradiating a titanium or titanium-alloy thin-plate substrate having a plate thickness of 2 to 100 μm with a laser beam and perforating a plurality of pores in a pore perforation section surrounded by a frame section. In the manufacturing method of this aspect, the pore perforation section, except for crosspieces which extend lengthwise and crosswise in continuity with the frame section and partition the pore perforation section into a plurality of parts, is irradiated with a laser beam having a pulse width of 10 nsec or less; pores are perforated which have a pore diameter calculated as an equivalent circular pore diameter of 1 to 50 μm and of which the center-to-center distance between adjacent pores is 2 to 200 μm; and a plurality of pore perforation cells, each of which is surrounded by the crosspieces and has a plurality of the pores perforated therein, are formed in the pore perforation section.

In the production methods of a porous plate for medical use of the second and third aspects, the size of the pore perforation cell surrounded by the crosspieces can be such that the inscribed circle of the cell is 0.5 to 5 mm in diameter. The width of the crosspieces can be 0.1 to 0.5 mm. In addition to the pores, second pores having a pore diameter calculated as an equivalent circular pore diameter of 80 to 220 μm can be perforated in the pore perforation cells dispersedly at a center-to-center distance of 2 to 4 mm.

The pore perforation cells surrounded by the crosspieces can each have a regular polygonal shape, and the pore perforation cells can be formed in a uniform distribution in the pore perforation section. Alternatively, the pore perforation cells surrounded by the crosspieces can each have a hexagonal shape with parallel opposite sides, and the pore perforation cells can be formed in a honeycomb distribution in the pore perforation section.

Advantageous Effects of Invention

The porous plate for medical use of the first aspect has the crosspieces which extend lengthwise and crosswise in continuity with the frame section and partition the pore perforation section into a plurality of parts, and the plurality of pore perforation cells each surrounded by the crosspieces. That is, the pore perforation section is formed of the plurality of pore perforation cells each of which is surrounded by the crosspieces and has a large number of small pores perforated therein. Thus, the lines sequentially connecting the adjacent pores are disrupted by the crosspieces while a certain elasticity is retained, so that bending of the porous plate along the array direction of the pores is suppressed. Moreover, development of cracks and ruptures is blocked by the presence of the crosspieces.

If the size of the pore perforation cell surrounded by the crosspieces is such that the diameter of the inscribed circle of the cell is 0.5 to 5 mm in diameter, it is possible to leave a large number of crosspieces while perforating such a number of pores as is sufficient for tissue regeneration medicine in each pore perforation cell. Thus, even if a local crack occurs, the crack stops at the crosspieces and does not reach the adjacent pore perforation cell, so that the crack can be restricted to a small area and prevented from leading to plate fracture. If the width of the crosspieces is set to 0.1 to 0.5 mm, it is possible to provide the porous plate with a moderate elasticity as well as to reliably fix the porous plate by driving fixing pins into the crosspieces.

According to the configuration in which, in addition to the pores perforated in the pore perforation cells, the second pores having a pore diameter calculated as an equivalent circular pore diameter of 80 to 220 μm are perforated in the pore perforation cells dispersedly at a center-to-center distance of 2 to 4 mm, it can be expected that, for example, cells which can generate a capillary as host-derived cells enter a region of high porosity maintained by the second pores and thereby form a nutrient supply channel through blood flow in a transplanted cultivated cell sheet. It is also possible to drive fixing pins through the second pores, so that a porous plate for medical use having both the function and convenience can be provided.

According to the configuration in which the pore perforation cells surrounded by the crosspieces each have a regular polygonal shape and the pore perforation cells are formed in a uniform distribution in the pore perforation section, or the configuration in which the pore perforation cells each have a hexagonal shape with parallel opposite sides and the pore perforation cells are formed in a honeycomb distribution in the pore perforation section, it is possible to suppress bending in a certain direction along the array of the pores and development of cracks, to uniformize the strength owing to the isotropic arrangement with a predetermined crosspiece width, and to provide the porous plate with an almost uniform elasticity against bending in an arbitrary direction.

Thus, the porous plate for medical use of the first aspect is useful as a porous plate for medical use which has overcome the problems peculiar to a porous plate having small pores perforated therein in high density.

In the manufacturing methods of a porous plate for medical use of the second and third aspects, the pores are perforated by irradiation with a laser beam of which the pulse width is determined on the basis of a heat diffusion length in the substrate when irradiated with a laser beam. Thus, according to these manufacturing methods, a porous plate substantially free from thermal effects can be provided. Moreover, in these manufacturing methods, since the pores are sequentially perforated by irradiating the substrate with a pulsed laser beam, it is possible to stably produce a porous plate having small pores perforated therein in high density.

In the manufacturing methods of a porous plate for medical use of the second and third aspects, a porous plate for medical use is manufactured by irradiating the pore perforation section, except for the crosspieces which extend lengthwise and crosswise in continuity with the surrounding frame section and partition the pore perforation section into a plurality of parts, with a laser beam, and forming the plurality of pore perforation cells each of which is surrounded by the crosspieces and has a plurality of the pores perforated therein. In the porous plate for medical use thus manufactured, the pore perforation section is formed of the plurality of pore perforation cells each of which is surrounded by the crosspieces and has a large number of small pores perforated therein. Accordingly, the lines sequentially connecting the adjacent pores are disrupted by the crosspieces while a certain elasticity is retained, so that bending of the porous plate along the array direction of the pores is suppressed. Moreover, the durability of the material against folding can be enhanced by the presence of the crosspieces.

If the heat diffusion length defining the pulse width is set to 1 μm or less, it is possible to provide a porous plate almost free from thermal effects of laser beam irradiation. If the pulse width of the radiated laser beam is set to 10 nsec or less, it is possible to provide a porous plate, on which thermal effects present substantially no problem with its use, for many materials used for tissue regeneration medicine such as titanium and alumina ceramics.

If the size of the pore perforation cell surrounded by the crosspieces is such that the inscribed circle of the cell is 0.5 to 5 mm in diameter, it is possible to leave a large number of crosspieces while perforating such a number of pores as is sufficient for tissue regeneration medicine in each pore perforation cell. Thus, even if a local crack occurs, the crack stops at the crosspieces and does not reach the adjacent pore perforation cell, so that the crack can be restricted to a small area and prevented from leading to plate fracture. If the width of the crosspieces is set to 0.1 to 0.5 mm, it is possible to provide the porous plate with a moderate elasticity as well as to reliably fix the porous plate by driving fixing pins into the crosspieces.

According to the configuration in which, in addition to the pores perforated in the pore perforation cells, the second pores having a pore diameter calculated as an equivalent circular pore diameter of 80 to 220 μm are perforated in the pore perforation cells dispersedly at a center-to-center distance of 2 to 4 mm, it can be expected that, for example, cells which can generate a capillary as host-derived cells enter a region of high porosity maintained by the second pores and thereby form a nutrient supply channel through blood flow in a transplanted cultivated cell sheet. It is also possible to drive fixing pins through the second pores, so that a porous plate for medical use having both the function and convenience can be provided.

According to the configuration in which the pore perforation cells surrounded by the crosspieces each have a regular polygonal shape and the pore perforation cells are formed in a uniform distribution in the pore perforation section, or the configuration in which the pore perforation cells each have a hexagonal shape with parallel opposite sides and the pore perforation cells are formed in a honeycomb distribution in the pore perforation section, it is possible to suppress bends in a certain direction along the array of the pores and development of cracks, to uniformize the strength owing to the isotropic arrangement with a predetermined crosspiece width, and to provide an almost uniform elasticity against bending in an arbitrary direction. If the width of the crosspieces is set to 0.1 to 0.5 mm, an effect of dividing a group of cells adhering to the pore perforation section into blocks can be expected, which makes it possible to cause the divided groups of cells to exhibit individually different physiological effects or to subject them to individually different pharmacological actions. Or it becomes possible to supply nutrients or drugs using the crosspieces as channels. Moreover, when cells having high extensibility, such as fibroblasts, develop by migrating over the plate, it is possible to achieve the effect of causing the cells to generate a pseudopod which traverses the crosspieces so as to extend across a perforated region divided by the crosspieces.

Thus, according to the manufacturing methods of a porous plate for medical use as has been described above, it is possible to manufacture a porous plate for medical use which has overcome the problems peculiar to a porous plate having small pores perforated therein in high density.

In the above description, the GTR technique has been shown as an example of tissue regeneration medicine. However, tissue regeneration guidance using the porous plate of the present invention is applicable to the guided bone regeneration (GBR) technique, a guided tissue regeneration technique for various organs, etc. for the purpose of tissue regeneration where, despite a certain level of regenerative capability, autonomous restoration of tissue is hindered due to its growth rate lower than the surrounding tissue.

In the porous plate for medical use thus manufactured and configured, the pores perforated in the substrate can have a pore diameter calculated as an equivalent circular pore diameter of 1 to 20 μm. The size of an opening which a normal human tissue cell can pass through is said to be approximately 10 μm in minimum diameter. However, passage of cells is considerably limited even when the actual size of the pore is larger. For example, in a porous plate with a large number of pores having a pore diameter of 20 μm perforated therein, it was experimentally confirmed that, in comparison with a large number of cells which adhered to and grew on the plate surface, a considerably smaller number of cells passed the pores. Accordingly, if the pore diameter of the pores is set to 1 to 20 μm, the barrier function of blocking entry of tissue can be sufficiently realized. Moreover, if the pore diameter of the pores is set to 1 to 10 μm, an almost perfect cell barrier can be realized.

BRIEF DESCRIPTION OF DRAWINGS

FIG. 6 is a view illustrating the workings of the porous plate for medical use.

FIGS. 7A, 7B, 7C, and 7D are schematic views showing examples of the shapes of the pores perforated in the porous plate for medical use.

FIGS. 16A and 16B are views showing another configuration example of the porous plate manufactured by the manufacturing method of the present invention, in which FIG. 16A is an external view of the porous plate and FIG. 16B is a partially enlarged view of the pore perforation section.

FIGS. 17A and 17B are views showing another configuration example of the porous plate manufactured by the manufacturing method of the present invention, in which FIG. 17A is an external view of the porous plate and FIG. 17B is a partially enlarged view of the pore perforation section.

DESCRIPTION OF EMBODIMENTS

Figure 2:
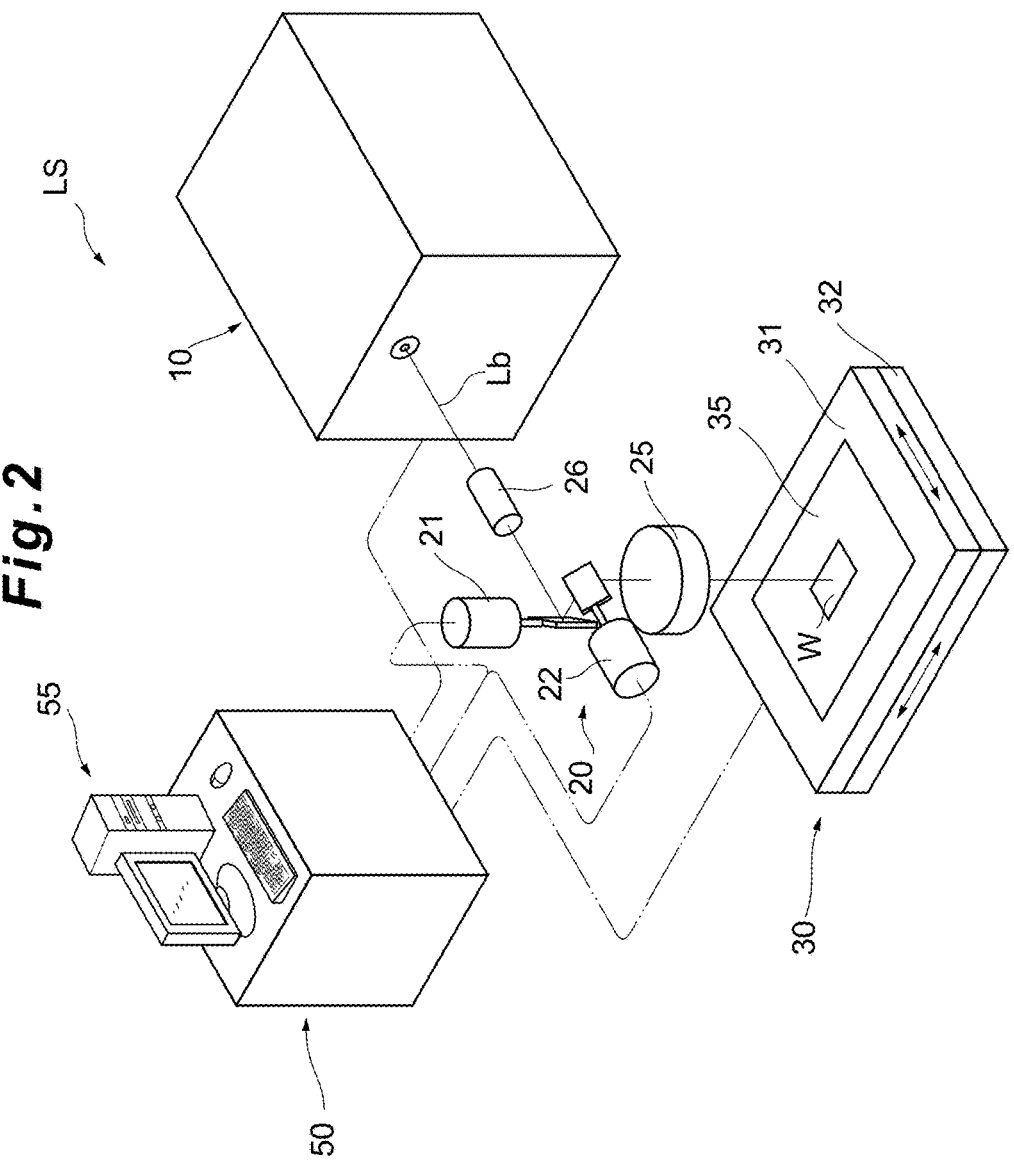
FIG. 2 is a schematic configurational view of a laser processing system shown as an example of a device suitable for manufacturing a porous plate.
Figure 3:
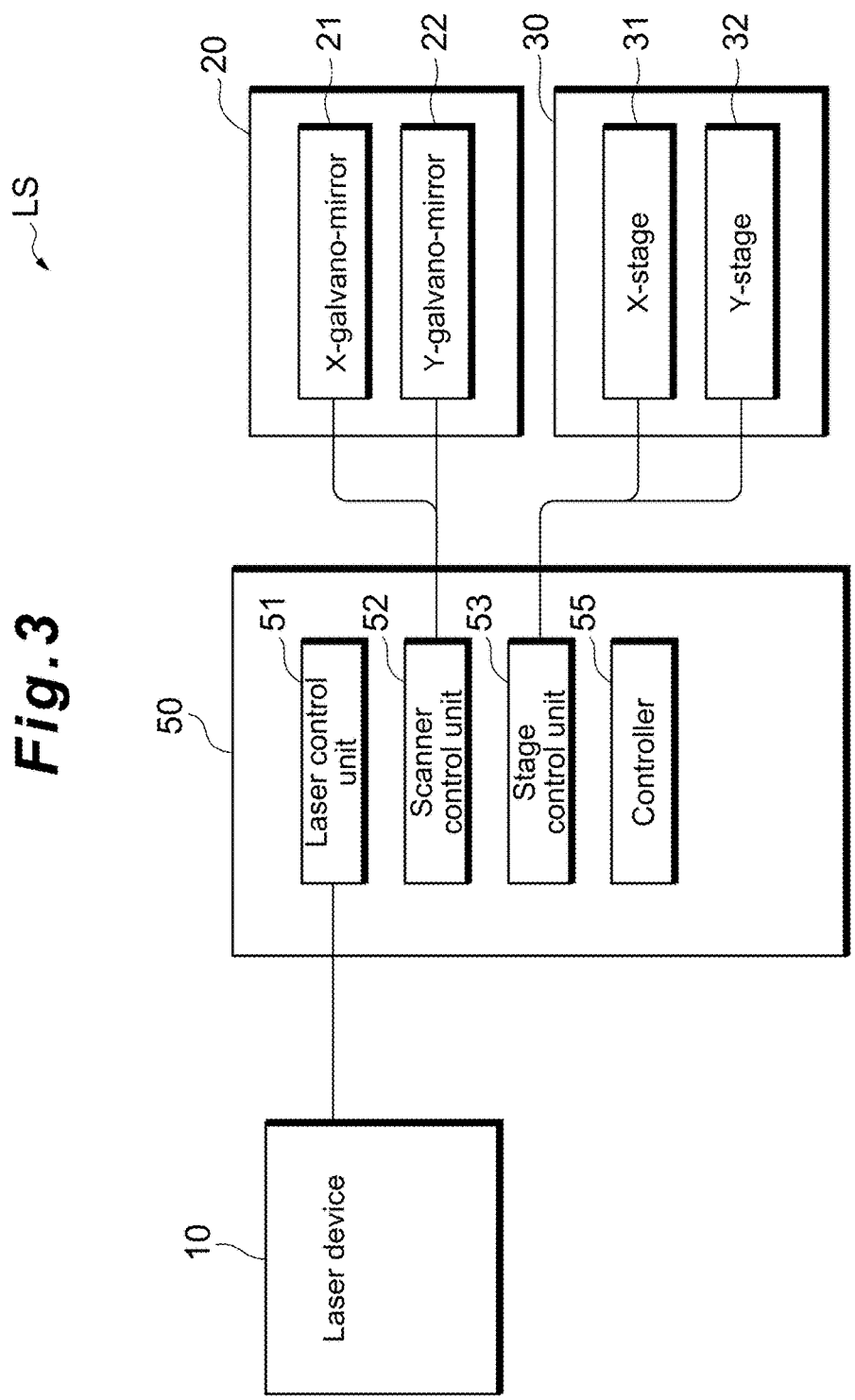
FIG. 3 is a block diagram of the laser processing system.

In the following, embodiments of the present invention will be described. FIG. 2 and FIG. 3 show the general configuration and a block diagram, respectively, of a laser processing system as an example of a device suitably used in a manufacturing method of a porous plate for medical use according to the present invention. First, the outline of the laser processing system will be described with reference to these drawings. The two-dot chain lines in FIG. 2 represent electrical signal lines such as control cables.

A laser processing system LS includes: a laser device 10 which outputs a laser beam Lb; a stage 30 which holds a workpiece W, which is the material of a porous plate, and moves the workpiece W in two directions, an X-direction and a Y-direction, perpendicular with each other in a horizontal plane; a beam scanner 20 and an fθ lens 25 which are provided on a light path to guide the laser beam Lb output from the laser device 10 to the workpiece W on the stage 30; and a control device 50 which controls the operation of the laser device 10, the beam scanner 20, the stage 30, etc.

The laser device 10 is configured to be able to output the short-pulsed laser beam Lb having a pulse width of 300 fsec to 100 nsec and an average power of approximately 100 mW to 5 W. The wavelength of the laser beam output from the laser device 10 can be selected from wavelengths from the infrared region where the wavelength is approximately 1 μm to the ultraviolet region where the wavelength is approximately 300 nm.

The optical system which guides the laser beam Lb output from the laser device 10 to the workpiece W held on the stage 30 is provided with, other than the beam scanner 20, a collimator 26 which collimates the laser beam Lb output from the laser device 10 into a parallel beam, a light guiding optical element (not shown) which guides the laser beam emitted from the collimator 26 to the beam scanner 20, and the like. The optical system may be further provided with a beam expander which adjusts the laser beam diameter, a polarization element which adjusts the polarization of the laser beam, and the like.

The beam scanner 20 is a device which scans the workpiece W held on the stage 30 with a laser beam, and in this configuration example, a scanning device which scans with a laser beam in the X- and Y-directions using a galvano-mirror (galvano-scanner) is shown as an example. That is, the beam scanner 20 is mainly composed of an X-galvano-mirror 21 which scans a laser beam in the X-direction and a Y-galvano-mirror 22 which scans a laser beam in the Y-direction on the workpiece W. A driver driving the X-galvano-mirror 21 and the Y-galvano-mirror 22 is provided in the control device 50.

The fθ lens 25 is a lens which focuses a laser beam deflected by the beam scanner 20 to the surface (image surface) of the flat workpiece W and converts an equiangular motion of the scanner into a uniform motion to scan on the workpiece W. In the laser processing system LS, an fθ lens of telecentric type is used which focuses and emits the laser beam, which has been deflected by the beam scanner 20 and entered the fθ lens 25, vertically to the surface of the workpiece W. Thus, pores perforated in the substrate are vertical to the surface of the substrate and have a uniform diameter regardless of the processing position, and a large number of pores can be perforated with high positional accuracy.

The stage 30 includes a chuck 35 which horizontally fixes and holds the workpiece W, an X-stage 31 which moves the workpiece W held by the chuck 35 in the X-direction, and a Y-stage 32 which moves the workpiece W in the Y-direction. The stage 30 may be further provided with a Z-stage which moves the workpiece W held by the chuck 35 in a Z-direction (vertical direction) perpendicular with the horizontal X-Y plane, a θ-stage which turns the chuck 35 around a Z-axis extending in the vertical direction, and the like.

The control device 50 includes a laser control unit 51 which controls the operation of the laser device 10, a scanner control unit 52 which controls the operation of the beam scanner 20, a stage control unit 53 which controls the operation of the stage 30, and a controller 55 which outputs command signals to the control units 51, 52, 53 on the basis of a control program set and stored therein in advance or a processing program read thereinto.

The laser control unit 51 controls the operation of the laser device 10 on the basis of a command signal output from the controller 55. Specifically, the laser control unit 51 generates in the laser device 10 a laser beam having a peak power, a pulse width, and a pulse period according to a pulse command signal output from the controller 55, and outputs the laser beam from the laser device 10 at an on/off timing according to an output command signal.

The scanner control unit 52 controls the operation of the beam scanner 20 on the basis of a command signal output from the controller 55. Specifically, the scanner control unit 52 controls the driving of the X-galvano-mirror 21 and the Y-galvano-mirror 22 according to a scanning command signal output from the controller 55, and focuses and radiates the laser beam to the workpiece at a position and a scanning rate and in a scanning track according to the scanning command signal. For example, when perforating a pore, which has a pore diameter close to the diameter of a focused beam spot, at a predetermined position of the workpiece W, the scanner control unit 52 controls the angular positions of the X-galvano-mirror 21 and the Y-galvano-mirror 22 such that the position irradiated with the laser beam coincides with the predetermined position. When perforating a pore, which has a quadrangular shape, star shape, etc., with reference to a predetermined position, the scanner control unit 52 controls the driving of the X-galvano-mirror 21 and the Y-galvano-mirror 22 such that the laser beam moves at a predetermined scanning rate and in a scanning track having a rectangular shape, a star shape, etc. with reference to the predetermined position.

The stage control unit 53 controls the operation of the stage 30 on the basis of a command signal output from the controller 55. Specifically, the stage control unit 53 drives the X-stage 31 and the Y-stage 32 according to a positional command signal output from the controller 55 to move the workpiece W held by the chuck 35 to a predetermined position. For example, upon completion of perforating of a region which can be processed through beam scanning by the beam scanner 20 (referred to as a scanning processing region), the stage control unit 53 moves the workpiece W to a position according to the positional command signal output from the controller 55, i.e., the position falling within the next scanning processing region, and holds the workpiece W at that position.

The controller 55 is configured on the basis of a personal computer, and includes: a display device which displays various pieces of information, such as the operation status and the setting conditions of each unit, and a selected processing program; a keyboard through which various pieces of information including information on a processing position are input, changed, etc.; and a mouse through which a reading operation of a processing program and CAD data, selection of processing conditions, etc. are performed.

Thus, according to the laser processing system LS of which the general configuration has been described above, a processing program is read in the controller 55, and selection, correction, etc. of various setting conditions are performed as necessary before laser processing is started. Accordingly, it is possible to focus and radiate a laser beam, of which the pulse conditions are set by the processing program, to a position set by the processing program, and perforate a pore of a shape set by the processing program.

Next, a manufacturing method of a porous plate for medical use using the laser processing system LS will be described. The manufacturing method of a porous plate to be shown as an example involves irradiating the workpiece W with a laser beam having a pulse width which is determined on the basis of a heat diffusion length in the workpiece when irradiated with a laser beam, and sequentially perforating pores which have a pore diameter calculated as an equivalent circular pore diameter of 1 μm to 50 μm and of which the center-to-center distance between adjacent ones is 2 μm to 200 μm.

Here, for the workpiece W forming the substrate of the porous plate, a highly biocompatible material having a thin plate shape, i.e., a dense and solid composition, instead of being porous or fibrous, is used. Examples of such a material include a thin plate made of a metal material, such as titanium, titanium alloy, or silver alloy, a thin plate made of an inorganic material, such as alumina ceramics, and a thin plate made of a polymer material, such as PTFE and polylactide.

Polymer materials, such as PTFE and polylactide, are materials of which there are already many examples of practical use in tissue regeneration treatment for alveolar bones by the GTR technique. When a thin-plate material made of such a polymer material is used as the workpiece W, i.e., the substrate of the porous plate, it is possible to reduce the thickness required for providing the same physical strength compared with the conventional barrier membrane made of the same material (e.g., PTFE).

When a biocompatible metal material is used as the substrate of the porous plate (workpiece W), it is possible to achieve a plate thickness of 2 to 100 μm while retaining the strength and the elasticity of the substrate, and thus the thickness can be further reduced compared with the porous plate made of a polymer material. In addition, it is possible to manufacture a porous plate which is easy to handle and more flexible than when an inorganic material, such as alumina ceramics, is used.

As a biocompatible metal material, various metal materials, such as titanium, titanium alloy, stainless steel, cobalt-chrome alloy, cobalt-chrome-molybdenum alloy, tantalum, zirconium, gold, platinum, and silver alloy, are available. Especially titanium and titanium alloy are widely used as a biocompatible metal material in both medical and dental fields, and there are many examples of their practical use in medical treatment. Thus, by using a titanium or titanium-alloy plate as the substrate of the porous plate, it is possible to manufacture a porous plate which is widely applicable in the field of tissue regeneration medicine.

Figure 1:
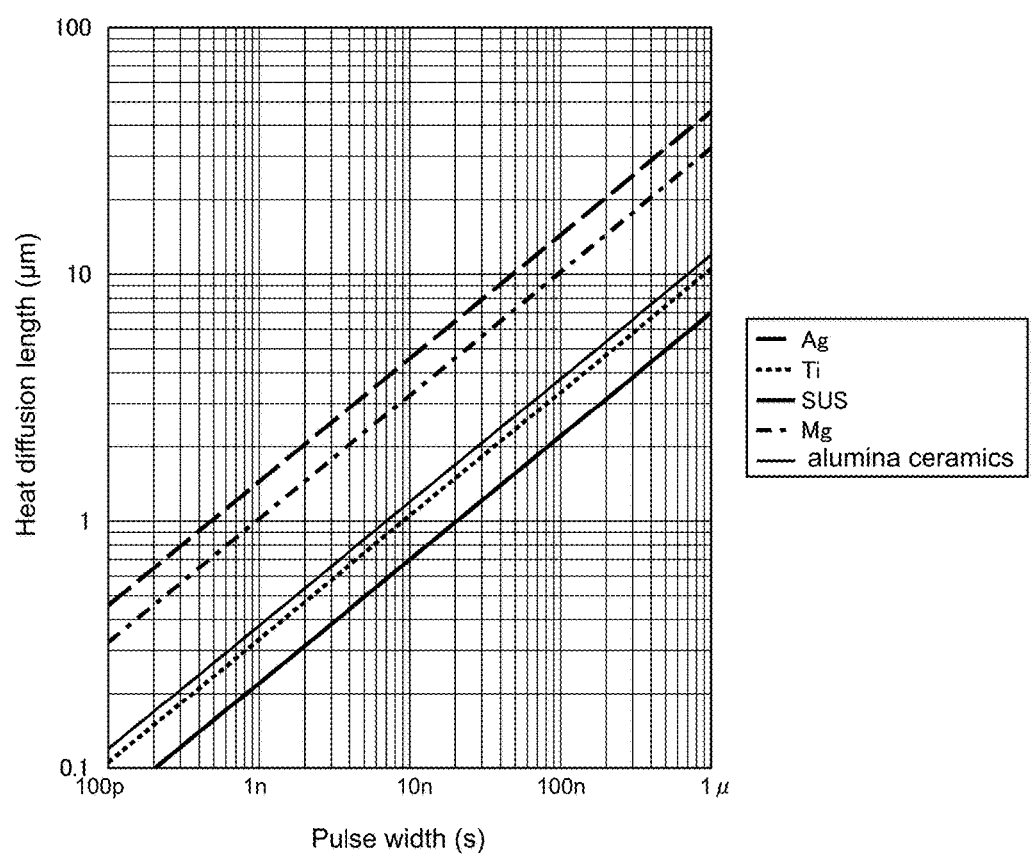
FIG. 1 is a graph showing the relation between the pulse width of a laser beam radiated to a substrate and the diffusion length of heat generated in the substrate as a result of irradiation with the laser beam (heat diffusion length).

In the manufacturing method of a porous plate shown as an example, pores are perforated by focusing and radiating a laser beam, which has a pulse width determined on the basis of a heat diffusion length in the workpiece when irradiated with a laser beam, to the workpiece W serving as the substrate of the porous plate. Here, the pulse width of the laser beam determined on the basis of the heat diffusion length in the substrate is obtained by the heat diffusion theory as described with reference to the formula (1) and FIG. 1, and a pulse width for achieving a desired value of the heat diffusion length can be obtained if the type of material of the workpiece W is known. Referring to FIG. 1 again, it can be seen that, when the type of material of the workpiece W is titanium, for example, the pulse width of the laser beam to be radiated can be set to 10 nsec or less to set the diffusion length of heat absorbed in the workpiece as a result of irradiation with a laser beam to 1 μm or less.

In this case, the form and the thickness of thermal effects occurring on the workpiece W due to heat absorption vary depending on the type of material of the substrate. However, as long as the heat diffusion length is 1 μm or less, a porous plate on which the thermal effects present no problem with its use can be manufactured. Since the pores are sequentially perforated by irradiating the workpiece W with a pulsed laser beam, it is possible to stably provide a porous plate having small pores perforated therein in high density. The conditions of the laser beam output from the laser device 10 are set in the controller 55, and a laser beam of the set pulse width, repetition period, and peak power is output from the laser device 10 and focused and radiated to the workpiece W.

For the size of the pores perforated in the workpiece W, an appropriate pore diameter can be set within the range of 1 to 50 μm as a pore diameter calculated as an equivalent circular pore diameter. In this case, if the pore diameter of the pore to be perforated is close to the size of the focused beam spot (e.g., when the pore diameter of the pore is approximately ϕ1 to 20 μm), the position at which the laser beam radiated to the workpiece W is focused (focal position) can be set to a height position according to the pore diameter, and a laser beam can be radiated with the X-galvano-mirror 21 and the Y-galvano-mirror 22 fixed at a position where the pore is to be perforated. On the other hand, when the pore diameter of the pore to be perforated is larger than the size of the focused beam spot (e.g., when the pore diameter of the pore is approximately ϕ10 to 50 μm), the focal position of the laser beam radiated to the workpiece W can be set to the surface or the inside of the workpiece W, and the X-galvano-mirror 21 and the Y-galvano-mirror 22 can be driven so as to move the laser beam in a motion trace according to the pore diameter.

For the center-to-center distance between adjacent pores, an appropriate pitch can be set within the range of 2 to 200 μm. Specifically, in the scanning processing region which can be processed through beam scanning by the beam scanner 20, a plurality of pores can be perforated at predetermined positions by controlling the angular positions of the X-galvano-mirror 21 and the Y-galvano-mirror 22, and thereby adjacent pores can be perforated at a predetermined pitch. Upon completion of perforating of the scanning processing region, the X-stage 31 and/or the Y-stage 32 of the stage 30 are driven to move the workpiece W to a position falling within the next scanning processing region. Then, a plurality of pores are perforated at predetermined positions through beam scanning by the beam scanner 20 performed at the new position. Thus, the pores can be perforated at a predetermined pitch over a wide area. The conditions related to these pores can also be set in the controller 55.

The controller 55 outputs command signals to the laser control unit 51, the scanner control unit 52, and the stage control unit 53 on the basis of a control program set and stored therein in advance or a processing program read thereinto, and controls the operation of the laser device 10, the beam scanner 20, and the stage 30 to sequentially perforate the pores in a positional region set by the processing program.

Figure 4:
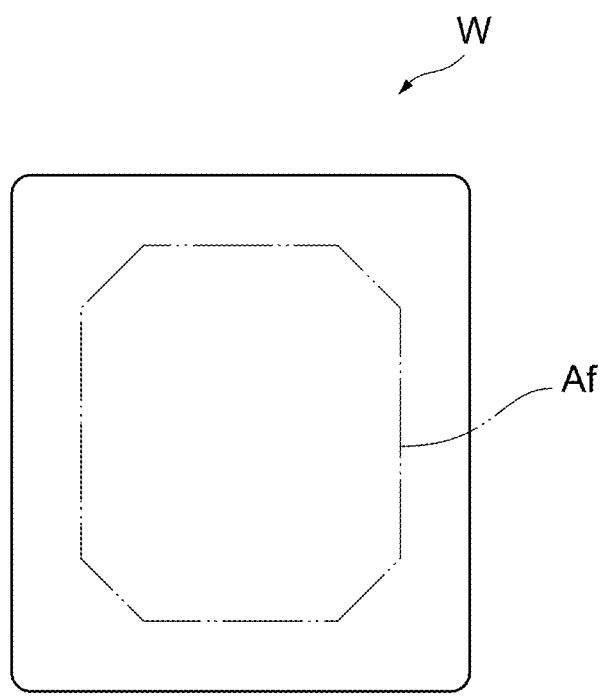
FIG. 4 is a view illustrating a region of a workpiece where pores are to be perforated.

Here, the perforation region of the pores set by the processing program is not the entire region of the workpiece W, but a center region Af (pore perforation section 63), as indicated by the two-dot chain lines in FIG. 4, except for a peripheral frame section of a predetermined width. Moreover, in the porous plate according to the present invention, the pores are not perforated over the entire perforation region Af surrounded by the two-dot chain lines; instead, the pores are perforated in divided regions of the perforation region Af partitioned by crosspieces which extend lengthwise and crosswise in continuity with the peripheral frame section, except in these crosspieces.

Figure 5:
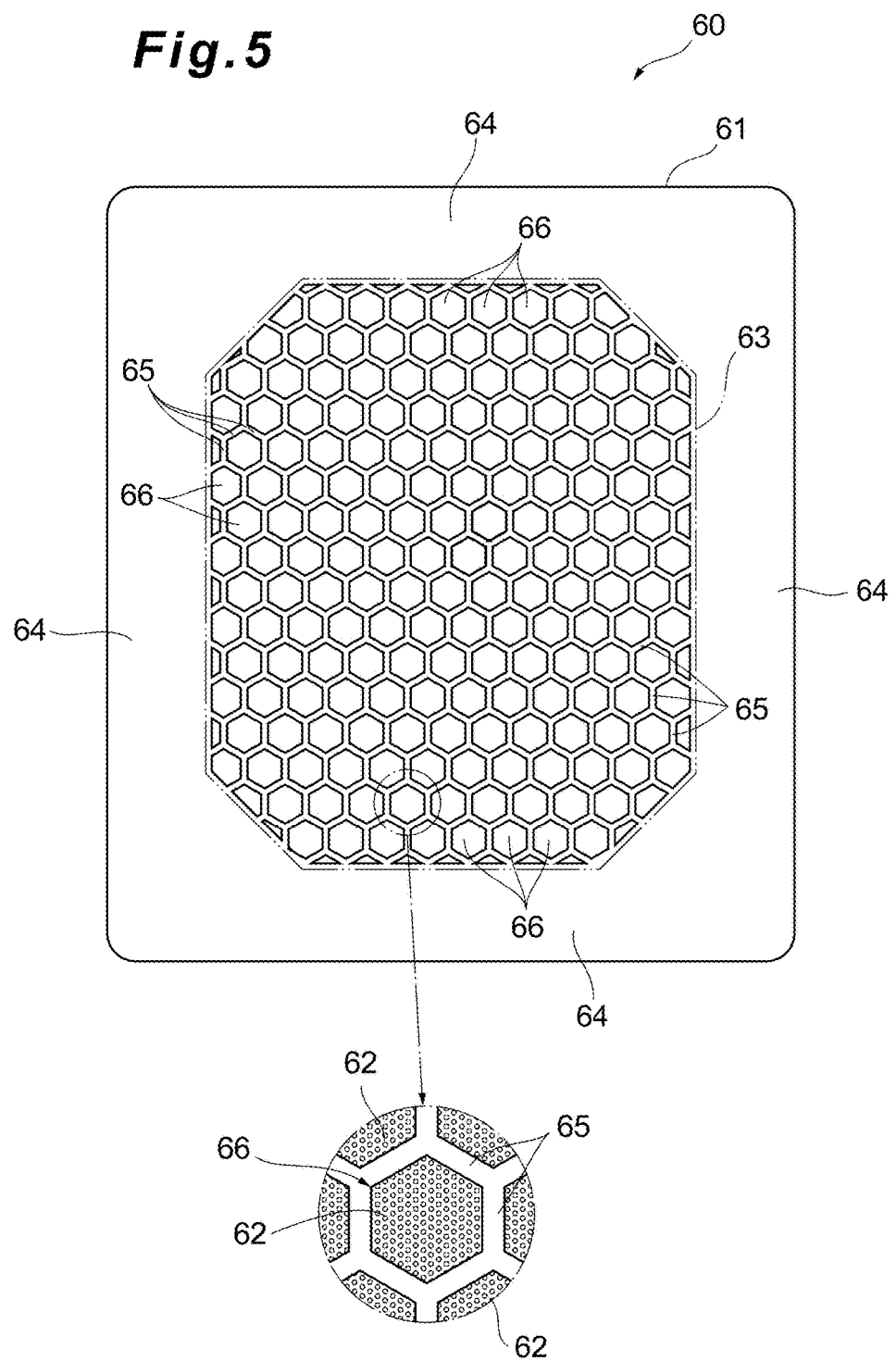
FIG. 5 is a schematic view of a porous plate for medical use shown as an example of a porous plate for medical use employing the present invention.

FIG. 5 shows a schematic view of a porous plate 60, which has a large number of pores perforated in the pore perforation region Af, as an example of the porous plate manufactured by the manufacturing method having been described above. The porous plate 60 is a thin-plate substrate 61 (workpiece W) having the pore perforation section 63 in which a large number of pores 62 are perforated and a frame section 64 surrounding the pore perforation section. The pore perforation section 63 is provided with crosspieces 65 which extend lengthwise and crosswise in continuity with the frame section 64 and partition the pore perforation section 63 into a plurality of parts. The plurality of pores 62 are sequentially processed and perforated in each of the divided regions surrounded by the crosspieces 65, and a plurality of pore perforation cells 66 each composed of a group of pores 62, 62, 62, and so on are formed.

FIG. 5 shows a configuration example in which the pore perforation cells 66 surrounded by the crosspieces 65 each have a regular hexagonal shape and the pore perforation cells 66 are formed in a honeycomb distribution pattern in the pore perforation section 63. The size and the arrangement of the pores 62 perforated in each pore perforation cell 66 are set such that the pore diameter calculated as an equivalent circular pore diameter is within the range of 1 to 50 μm and the center-to-center distance between the adjacent pores 62, 62 is within the range of 2 to 200 μm. For example, the size and the arrangement are set such that the pore diameter is 1 μm and the center-to-center distance is 2 μm; the pore diameter is 10 μm and the center-to-center distance is 50 μm; the pore diameter is 20 μm and the center-to-center distance is 100 μm; or the pore diameter is 50 μm and the center-to-center distance is 200 μm. The center-to-center distance between the adjacent pores 62, 62 can be set appropriately within the range of 2 to 200 μm on the condition that the pores do not connect with each other (each is an independent pore). If the center-to-center distance is set within such a range that the heat diffusion lengths of the pores do not overlap, it is possible to suppress possible tissue transformation, deformation, etc. due to heat and obtain a high-density porous plate.

Here, when the pore diameter of the pore 62 is set within the range of 30 to 50 μm, it is possible to obtain a cell passage suppression effect approaching the effect achieved by the conventionally-used barrier membrane made of a polymer material in the form of a sintered body or fibers. On the other hand, since the porous plate 60 of this configuration has a simple perforated filter structure formed by perforating the pores of the above pore diameter through the thin-plate substrate 61, the porous plate 60 can have a smaller plate thickness than the conventional barrier membrane. Moreover, local infection due to the growth of bacteria can be prevented highly effectively.

If the pore diameter of the pores 62 is set within the range of 1 to 20 μm, it is possible to exert a barrier function of blocking passage of human cells which is comparable to the function achieved by the conventional barrier membrane, as well as to significantly improve the function of allowing passage of bioactive substances which control growth and differentiation of cells, nutrients, and gas components (referred to conveniently as elements and components).

Moreover, if the pore diameter of the pores is set within the range of 1 to 10 µm, it is possible to realize an almost perfect cell barrier as well as to obtain a favorable permeability of nutrients. FIG. 6 schematically shows the workings of the porous plate 60 which is the thin-plate substrate 61 having a large number of pores 62 of a pore diameter within the above range (e.g., φ2 µm) perforated therein. As shown, a cell 70 in contact with the porous plate 60 cannot move through the pore 62 which has a smaller diameter than the cell 70. On the other hand, the elements and components 72, such as bioactive substances, nutrients, and gas components, can move freely through the pores 62.

With such a porous plate sealing organ- or tissue-derived cells and lying adjacent to the blood vessel circulation system, the sealed cells can functionally collaborate with the blood circulation system inside a body to exchange nutrients, cytokines, and gas. Thus, the porous plate can also function as an artificial organ or tissue. Moreover, it is also possible to maintain a place for a regenerated organ by making a space inside a body, and accommodate an artificial organ or tissue in that space.

In the simple filter model as described above, when the pore diameter of the pores 62 is larger than a cell, a mass of cells may flow out through the pores. However, according to an experiment with periodontal membrane-derived cells, in a porous plate having a pore diameter of 20 µm, for example, a large number of cells adhered to the plate surface and developed and grew profusely. The pores 62 were used exclusively as an anchor on which the cell bodies were supported, and almost no cells were found to have entered and permeated the pores 62. That is, even when the pore diameter of the pores 62 is so large that individual cells can pass therethrough, the pores 62 actually act as an anchor for the cells and act substantially as a cell barrier.

The cells adhering to the porous plate are fixed with the pseudopods of the cell bodies hanged on the inlet (pore edge) of the pores 62 as if they were suspended rings. This means that the cells are more likely to be anchored as the perforation pitch of the pores 62 is smaller. Accordingly, when the center-to-center distance between the pores 62 is up to approximately 100 µm, the cells use the pores 62 as an anchor by somehow stretching the cell bodies across two adjacent pores 62, 62, but when the distance between the pores exceeds 200 µm, the pores 62 no longer serve as an anchor and the cell adhesion effect decreases significantly. Therefore, the center-to-center distance between the pores 62 is preferably 100 µm or less, more preferably 50 µm or less, and even more preferably 30 µm or less. This is because the cell adhesion effect is clearly recognizable if the center-to-center distance is set to 50 µm or less, and the cell adhesion effect increases significantly if the center-to-center distance is set to 30 µm or less.

In the porous plate 60 of the present invention, the pore perforation section 63, which is used by being cut out into an appropriate shape at the time of operation for tissue regeneration medicine, is formed by the plurality of pore perforation cells 66 which are each surrounded by the crosspieces 65 and spread in the plane direction of the substrate 61. In other words, the large number of pores 62 perforated in the pore perforation section 63 are perforated in high density in the unit of pore perforation cell, and the pores 62 are separated from each other by the crosspieces 65 between adjacent pore perforation cells.

Accordingly, in a porous plate in which the pores 62 are perforated in high density in the pore perforation section 63 without the crosspieces 65, any attempt to deform the piece which is cut out from the pore perforation section 63 into an appropriate size according to a treatment region (referred to conveniently as an isolation piece) may cause bending along the array direction of the pores 62. By contrast, in the porous plate 60 of this configuration, the array of the pores 62 is disrupted by the crosspieces 65 while a certain elasticity is retained, so that bending of the isolation piece is suppressed. Moreover, when the plate is bent, development of cracks and ruptures in the array direction of the pores, which serve as a starting point of material fracture, is blocked, so that the durability of the material against folding can be enhanced. Furthermore, by anchoring a wire frame etc. for setting the shape of the isolation piece using the crosspieces 65, it becomes also possible to enhance the shapability of the isolation piece while preventing generation of cracks due to embrittlement of the pore perforation cells 66.

Here, the size of the pore perforation section 63 (the size of the region edged with the frame section 64), the size of the pore perforation cells 66, the width of the crosspieces 65, etc. can be appropriately set according to the site of tissue regeneration medicine using the porous plate, the size of the affected area, etc.

For example, when the porous plate is used as a barrier membrane for the already-described GTR technique, the size of the pore perforation section 63 is set to approximately 10 to 40 mm on a side, and the size of the pore perforation cell 66 is set such that the inscribed circle of the cell is approximately 0.5 to 5 mm in diameter. The width of the crosspieces 65 edging the pore perforation cells 66 is set to approximately 0.1 to 0.5 mm.

If the size of the pore perforation cell 66 is set such that the inscribed circle of the cell is 0.5 to 5 mm (more preferably approximately 0.8 to 2 mm) in diameter, when the isolation piece is cut out from the pore perforation section 63 into an appropriate size according to the treatment region, the isolation piece as a whole can be left with a large number of crosspieces 65 while having such a number of pores 62 as is sufficient for tissue regeneration medicine in the pore perforation cell 66. Therefore, even if bends, cracks, etc. occur during shaping of the isolation piece, expansion thereof can be suppressed to a small range of 0.5 to 5 mm. Thus, it is possible to provide a porous plate which is highly resistant to damage and easy to use. Moreover, if the width of the crosspieces is set to 0.1 to 0.5 mm, it is possible to provide the isolation piece with a moderate elasticity as well as to reliably fix the isolation piece by driving fixing pins into the crosspieces 65.

In the porous plate 60, the pore perforation cells 66 surrounded by the crosspieces 65 each have a regular hexagonal shape and are formed in a honeycomb arrangement pattern in the pore perforation section 63. Accordingly, it is possible not only to suppress bending in a certain direction along the array of the pores 62 and development of cracks, but also to provide a uniform elasticity against bending in an arbitrary direction when the isolation piece is deformed into a desired shape.

While the configuration in which the pore perforation cells 66 each have a regular hexagonal shape has been shown as an example, hexagons of which the length of one pair of opposite sides of three pairs of parallel opposite sides is longer than the length of the other two pairs of opposite sides may be disposed in a honeycomb shape (in a state where the hexagons are arranged without gap as in the case of regular hexagons). The size of the pore perforation cells 66, the width of the crosspieces 65, the size and the arrangement (perforation density) of the pores 62 perforated in each pore perforation cell 66, etc. can be set to appropriate values according to the tissue, the site, etc. to be regenerated using the porous plate 60.

While the case where the pores 62 have a circular shape in a plan view of the substrate 61 seen from the upper surface side (or the lower surface side) has been described, the pores can have other shapes. For example, as shown in FIGS. 7A to 7D as examples of other shapes of the pores, pores of arbitrary shapes, such as (a) triangular pores 62*a*, (b) quadrangular pores 62*b*, (c) hexagonal pores 62*c*, and (d) star-shaped pores 62*d*, can be perforated. If the effect of the shape of the pores is confirmed in cell tissue regeneration, the optimal shape can be adopted. In the case of the pores of these shapes, the size of the pores is set such that the pore diameter calculated as an equivalent circular pore diameter is 1 to 50 µm as described above. In the case of these pores 62*a* to 62*d*, the pore diameter calculated as an equivalent circular pore diameter can be specified as the diameter of the inscribed circle of each shape.

Figure 8:
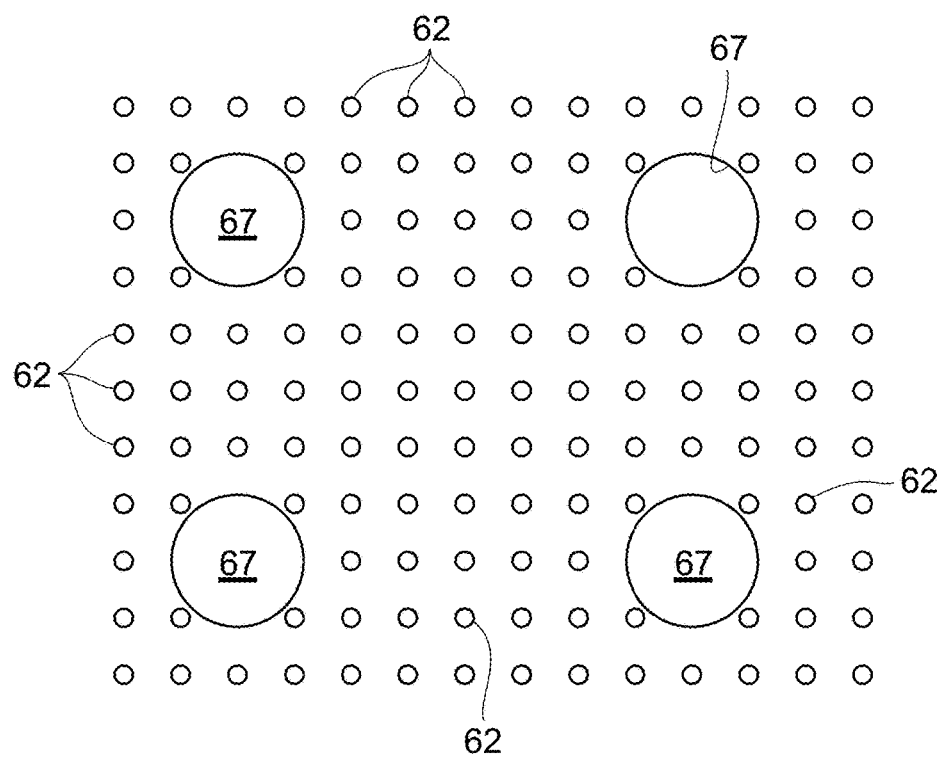
FIG. 8 is a schematic view showing a configuration example of a porous plate for medical use in which second pores are perforated in a pore perforation cell.

FIG. 8 shows another perforation pattern of the pores. As shown, it is also a preferable form in which, in addition to the pores (referred to as first pores) 62, 62*a* to 62*d* having been described above, second pores 67 having a pore diameter calculated as an equivalent circular pore diameter of approximately 80 to 220 µm are perforated in the pore perforation cells 66 dispersedly at a center-to-center distance of 2 to 4 mm. The second pores 67 serve to guide blood vessels through the porous plate, and allow passage of blood vessels, which are present before eventually becoming capillaries and supplying tissue regions with nutrients, i.e., of arterioles.

Since the diameter of an arteriole is approximately 100 to 200 µm, if set to 80 to 220 µm (e.g., 200 µm) in pore diameter, the second pores can be expected to guide arterioles and form a nutrient supply channel through blood flow. If the perforation pitch of the second pores 67 is set to 2 to 4 mm (e.g., 3 mm), it is possible to preserve the cell barrier function of the porous plate which consists mainly of the first pores, and to avoid excessive adhesion of the porous plate to tissue.

It is also possible to provide porous plate in an appropriate form according to the treatment site, the method of fixation to the peripheral tissue, etc., such as a porous plate in which the pore diameter of the pores 62 gradually changes from a center part toward a peripheral part of the pore perforation cell 66, a porous plate in which the perforation density of the pores 62 varies between the center part and the peripheral part, and a porous plate in which the pore diameter of the pores 62 varies among the pore perforation cells 66. For example, in the pore perforation cells 66 located in a region of 60% of the center part of the pore perforation section 63, pores having a pore diameter of 1 µm are perforated at a center-to-center distance of 2 µm; in the pore perforation cells 66 located in a region of 25% surrounding the center part, pores having a pore diameter of 2 µm are perforated at a center-to-center distance of 5 µm; and in the pore perforation cells 66 located in a region of 15% further on the peripheral part, pores having a pore diameter of 5 µm are perforated at a center-to-center distance of 10 µm. Thus, the size and the arrangement of the pores can be set arbitrarily.

In the configuration described above as an example, the pore perforation cells 66 surrounded by the crosspieces 65 each have a hexagonal shape with parallel opposite sides and are disposed in a honeycomb shape in the pore perforation section 63. However, the shape and the arrangement pattern of the pore perforation cells 66 can be changed appropriately.

Figure 9A:
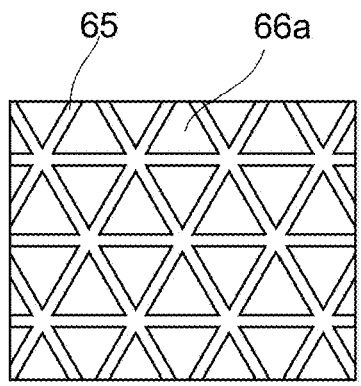
FIGS. 9A, 9B, 9C, 9D, 9E, and 9F are schematic views showing other configuration examples of a pore perforation section.
Figure 9B:
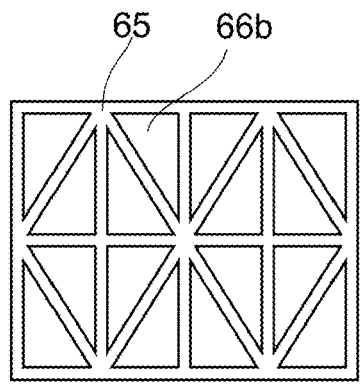
Figure 9C:
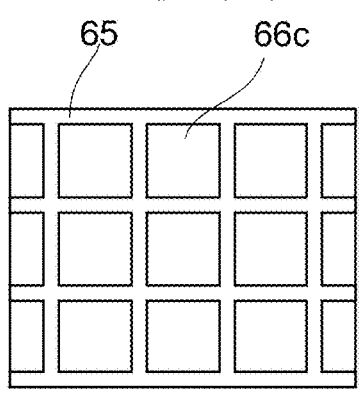
Figure 9D:
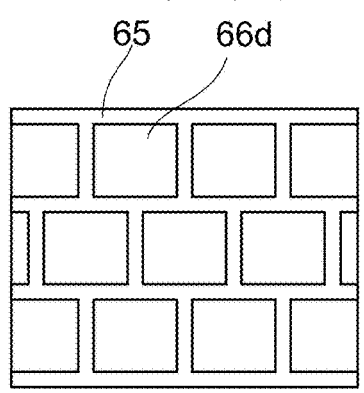
Figure 9E:
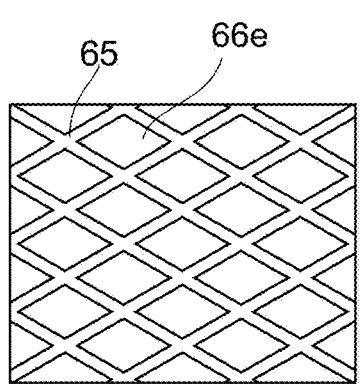
Figure 9F:
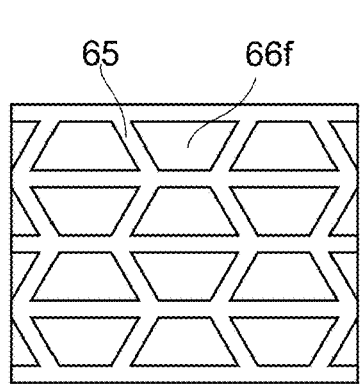

FIGS. 9A to 9D show other configuration examples of the pore perforation section 63. FIG. 9A is a configuration example in which pore perforation cells 66*a* have a regular triangular shape, and are arranged with the bases and the apexes of the adjacent pore perforation cells 66*a*, 66*a* respectively facing each other. FIG. 9B is a configuration example in which pore perforation cells 66*b* have a right triangular shape, and are arranged with the corresponding sides of the adjacent pore perforation cells 66*b*, 66*b* facing each other. FIG. 9C is a configuration example in which pore perforation cell 66*c* have a square shape, and the plurality of pore perforation cells 66*c*, 66*c*, and so on are arranged in a lattice shape. FIG. 9D is a configuration example in which pore perforation cells 66*d* have a square shape, and the plurality of pore perforation cells 66*d*, 66*d*, and so on are arranged in a staggered manner. FIG. 9E is a configuration example in which pore perforation cells 66*e* have a rhombic shape, and the plurality of pore perforation cells 66*e*, 66*e*, and so on are arranged with the oblique sides facing each another. FIG. 9F is a configuration example in which pore perforation cells 66*f* have a trapezoidal shape, and are arranged with the upper bases and the lower bases of the adjacent pore perforation cells 66*f*, 66*f* respectively facing each other.

For all the configuration examples of FIGS. 9A to 9F, a large number of pores 62, which have a pore diameter calculated as an equivalent circular pore diameter of 1 to 50 µm and of which the center-to-center distance between adjacent pores 62, 62 is 2 to 200 µm, are perforated in each pore perforation cell.

In the porous plates of such configurations as shown in each FIG. 9 as examples, too, the array of the pores 62 is disrupted by the crosspieces 65 formed between the pore perforation cells while a certain elasticity is retained, so that bending of the isolation piece cut out from the pore perforation section is suppressed. Moreover, development of cracks and ruptures is blocked by the presence of the crosspieces 65, so that the durability of the material against folding can be enhanced. As can be seen with reference to FIGS. 9A to 9F, the shape and the arrangement pattern of the pore perforation cells 66 can be set appropriately. For example, polygons with more than four sides can be combined, or the shape of the pore perforation cells shown in FIGS. 9C and 9D may be changed to an arbitrary quadrangular shape such as a rectangle or a parallelogram. Moreover, pore perforation cells of different shapes may be combined, for example, regular pentagons and regular hexagons may be combined in a soccer ball-like array pattern, or pore perforation cells having a circular shape or an elliptical shape may be arranged in an appropriate array pattern.

Figure 10:
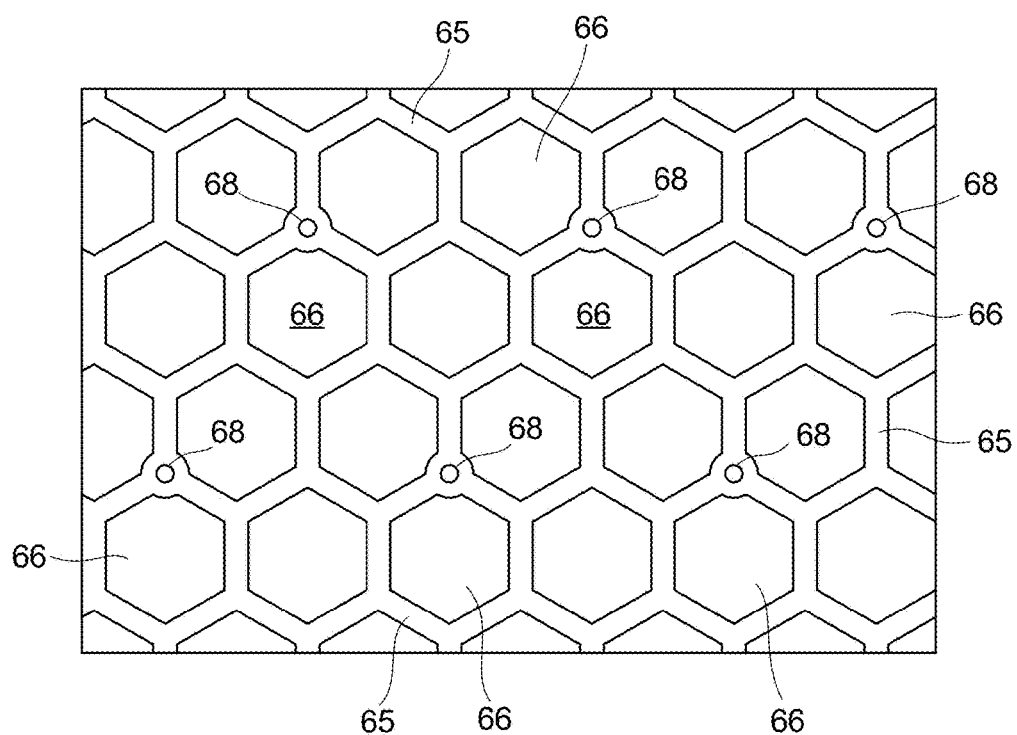
FIG. 10 is a schematic view of a configuration example in which third pores, through which fixing pins for fixing the porous plate for medical use are driven, are perforated in crosspieces.

FIG. 10 is a configuration example in which third pores 68 through which fixing pins are driven are perforated dispersedly in the crosspieces 65. In this configuration example, a configuration is shown as an example in which the third pores 68 having a pore diameter of 0.1 to 0.3 mm are perforated in the crosspieces 65 dispersedly at a center-to-center distance of 2 to 4 mm. In this configuration example, the third pores 68, which have the above pore diameter and through which the fixing pins are driven, are perforated in the crosspieces 65 edging the regular hexagonal pore perforation cells 66, at the apex of every other pore perforation cells 66, 66, and so on which are disposed continuously in the crosswise direction. In addition, the third pores 68, which have the above pore diameter and through which the fixing pins are driven, are perforated in the crosspieces 65 at the apex of every other pore perforation cells 66, 66, 66, and so on which are disposed continuously in the lengthwise direction. In this case, the third pores 68 are disposed at the above intervals which are uniform in the lengthwise and crosswise directions. Thus, it is possible to provide a porous plate of which the convenience of fixing the isolation piece, cut out from the pore perforation section 63, by driving the fixing pins thereinto is enhanced.

Figure 11:
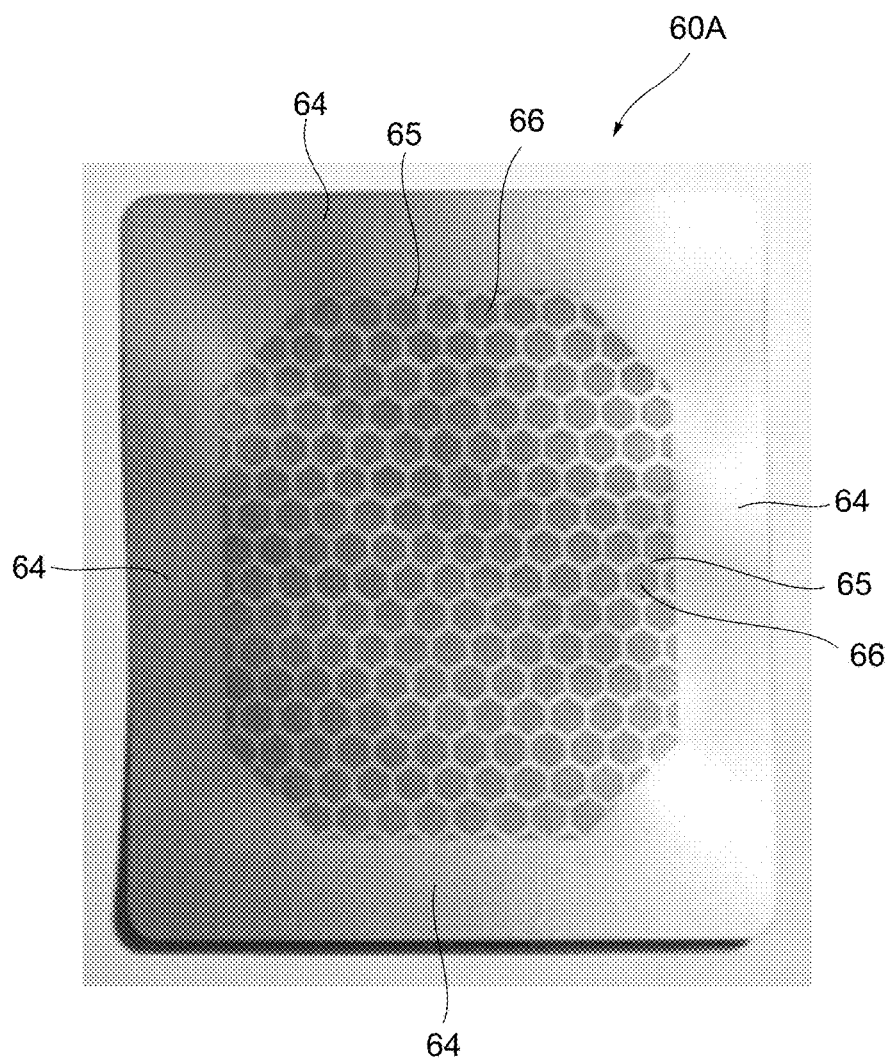
FIG. 11 is an external view (overall observation image) of a porous plate for medical use shown as an example of a porous plate manufactured by a manufacturing method of the present invention.
Figure 12:
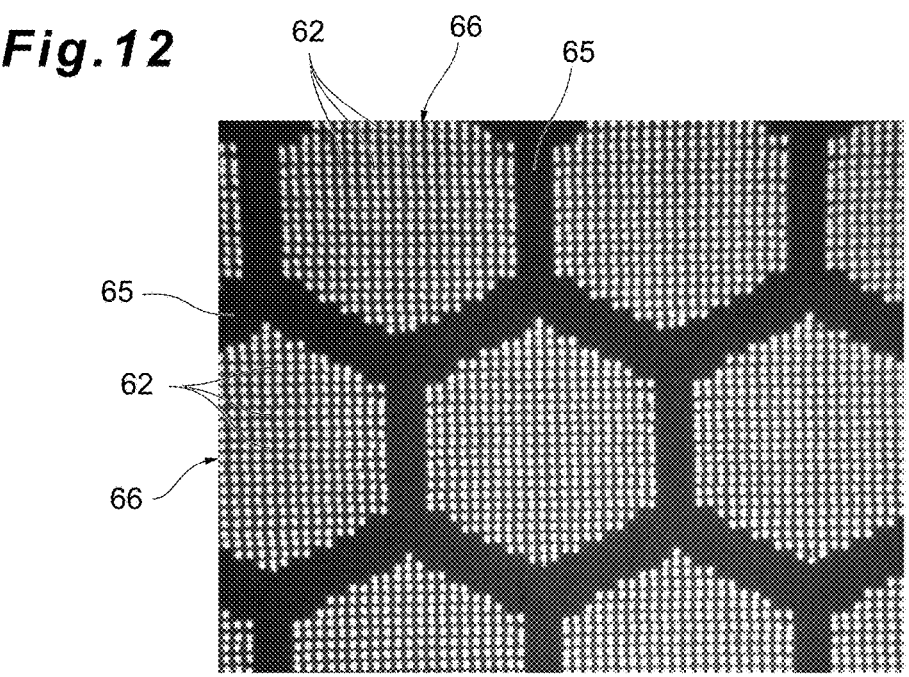
FIG. 12 is a partially enlarged view (enlarged observation image) of a configuration example of the pore perforation section in the porous plate for medical use shown in FIG. 11.
Figure 13:
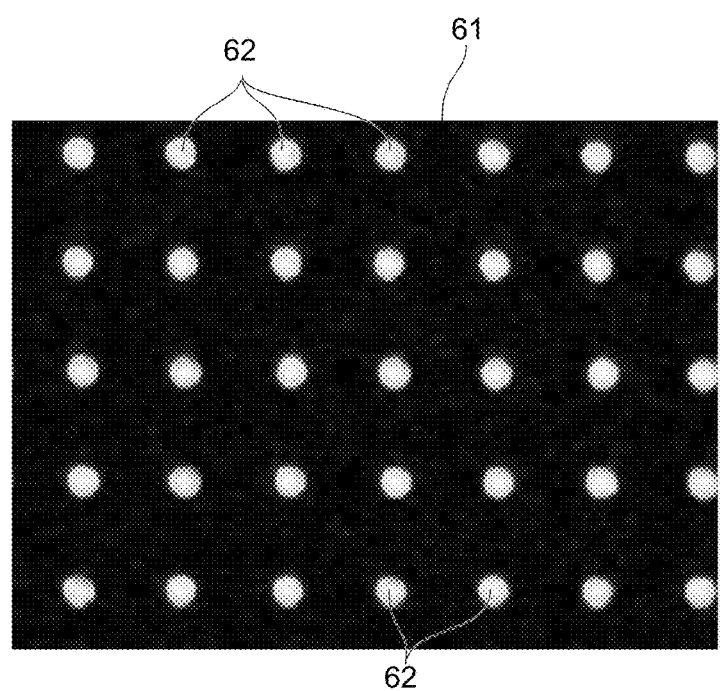
FIG. 13 is a partially enlarged view (enlarged transmission observation image) showing a perforation state of the pores perforated in the pore perforation cell of the pore perforation section shown in FIG. 12.

Next, a more specific configuration example of the porous plate manufactured by the manufacturing method of the present invention will be described. FIG. 11 is an external view (overall observation image) of a sample porous plate 60A manufactured by the manufacturing method of the present invention. FIG. 12 is a partially enlarged view (enlarged observation image) of the pore perforation section 63 in the porous plate 60A shown in FIG. 11. FIG. 13 is a partially enlarged view (enlarged transmission observation image) showing a perforation state of the pores 62 perforated in the pore perforation cell 66 of the pore perforation section 63 shown in FIG. 12.

This porous plate 60A is the substrate 61 of a titanium (pure titanium for medical use) having a plate thickness of 20 μm in which the plurality of regular-hexagonal pore perforation cells 66 having a distance between opposite sides of 1 mm and the width of the crosspieces 65 of 200 μm are formed in a honeycomb distribution in the pore perforation section 63. In each pore perforation cell 66, a large number of pores 62 having a center-to-center distance (perforation pitch) in the lengthwise and crosswise directions of 50 μm and an effective opening diameter of 20 μm are perforated.

Generally, the opening diameter of a pore perforated by laser processing is smaller in the lower surface of the substrate 61 at which a laser beam exits than in the upper surface of the substrate 61 to which the laser beam is radiated. Therefore, the present inventors observed the pore perforation section 63 under a transmission light microscope, and defined the effective opening diameter as the opening diameter (i.e., the minimum diameter of the pore 62) measured in a transmission light image. The effective opening diameter was approximately 20 μm±5 μm.

An actual measurement of the width of the crosspieces 65 in the observation image shown in FIG. 12 found that the width of the crosspieces 65 extending in the lengthwise direction (the upper-lower direction in FIG. 12) was about 180 μm, and the width of the crosspieces 65 extending obliquely in the crosswise direction was approximately 240 μm. This difference is due to the fact that the pores 62 perforated in the pore perforation cells 66 were perforated in a lattice shape at a regular pitch in the lengthwise and crosswise directions.

Figure 14:
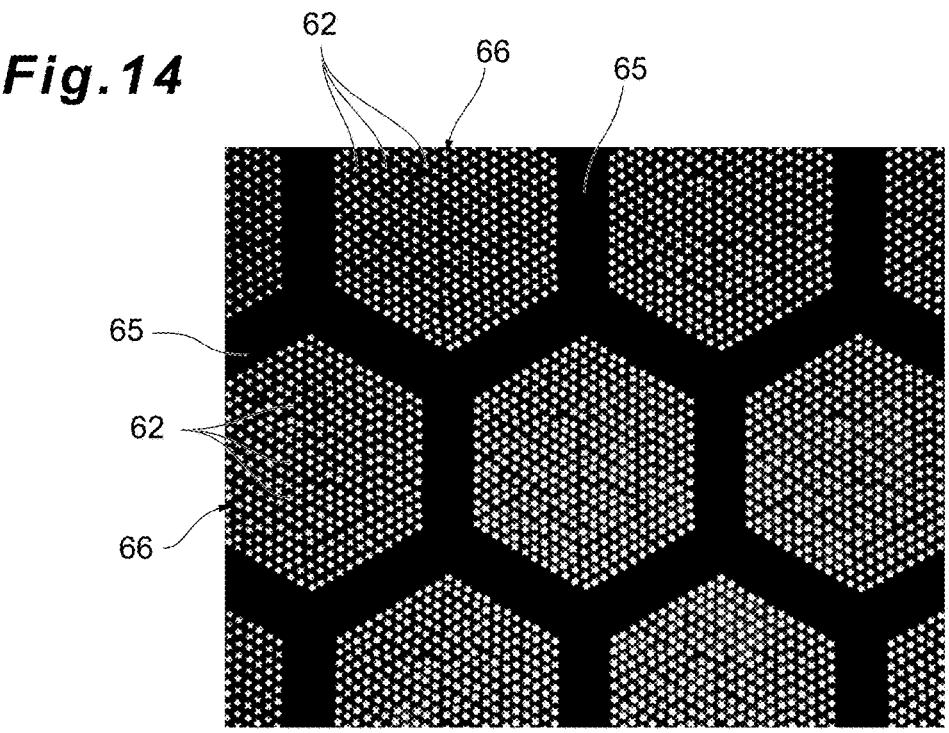
FIG. 14 is a partially enlarged view (enlarged observation image) of another configuration example of the pore perforation section in the porous plate for medical use shown in FIG. 11.
Figure 15:
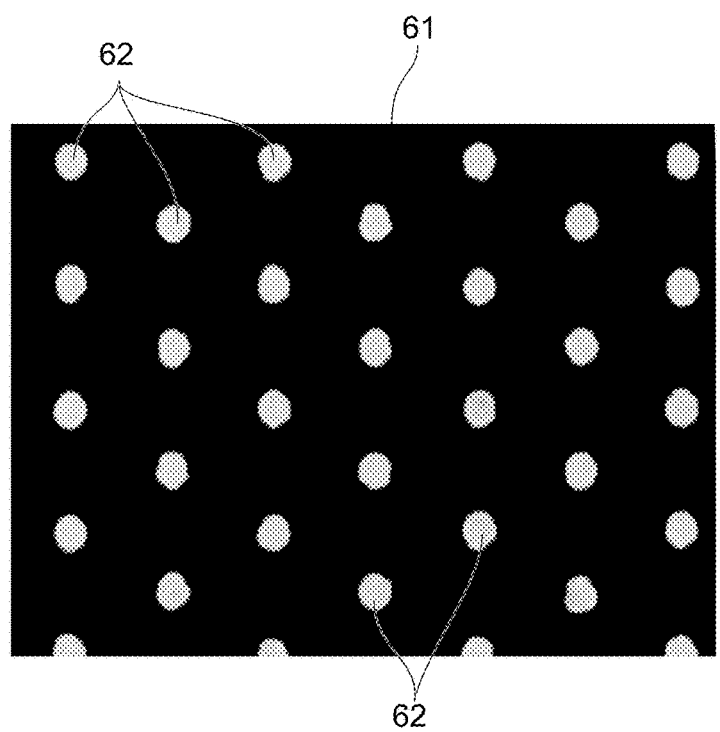
FIG. 15 is a partially enlarged view (enlarged transmission observation image) showing a perforation state of the pores perforated in the pore perforation cell of the pore perforation section shown in FIG. 14.

FIG. 14 shows another configuration example (enlarged observation image) of the pore perforation section 63 in the porous plate 60A shown in FIG. 11, and FIG. 15 shows a partially enlarged view (enlarged transmission observation image) of the pore perforation section 63. As can be understood through a comparison between FIG. 12 and FIG. 14 and between FIG. 13 and FIG. 15, in the foregoing configuration example, the pores 62 are perforated at the lattice points of the square lattice (at the corners of the squares of 50 μm on a side), while in this configuration example, the pores 62 are perforated at the lattice points of a triangular lattice (at the corners of the regular triangles of 50 μm on a side). The shape and the dimensions of the pore perforation cell 66 are the same as those of the foregoing configuration example.

According to such a configuration, since the pores 62 are arrayed along each side of the regular-hexagonal pore perforation cells 66, the width of the crosspieces 65 can be uniformized regardless of the extension direction and the position of the crosspiece 65 (see the partially enlarged view in FIG. 5). Moreover, since the pore density per unit area is increased, the number of pores 62 perforated in one pore perforation cell 66 is increased, and the opening area of the pores in the pore perforation cell 66 is increased by about 10% versus the square lattice array.

Figure 16A:
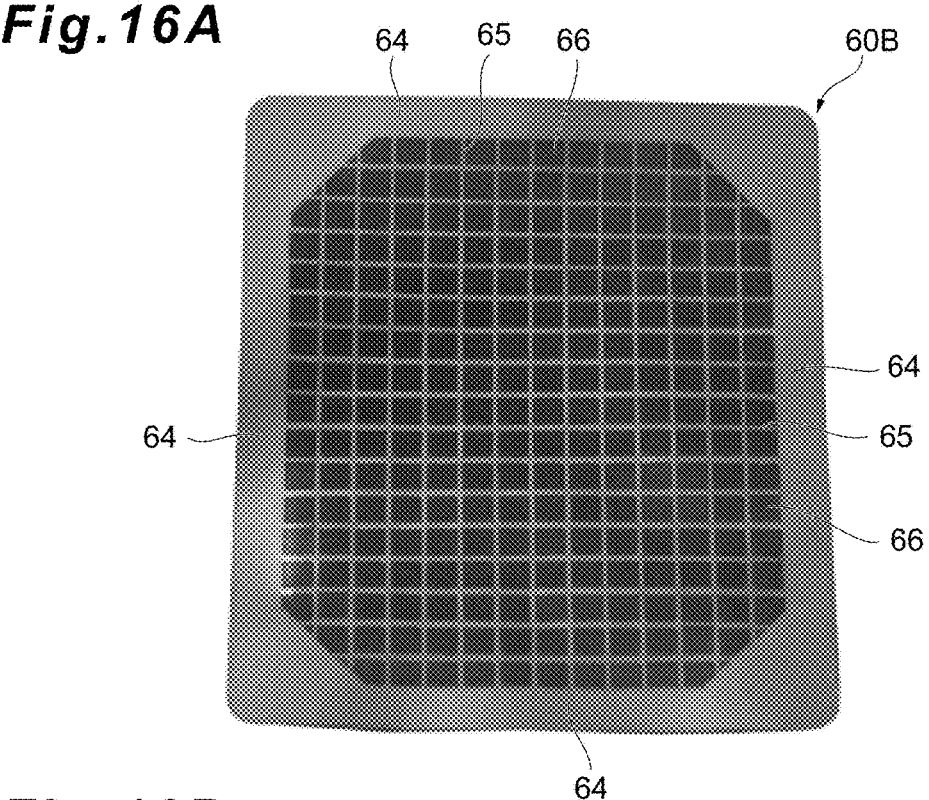
Figure 16B:
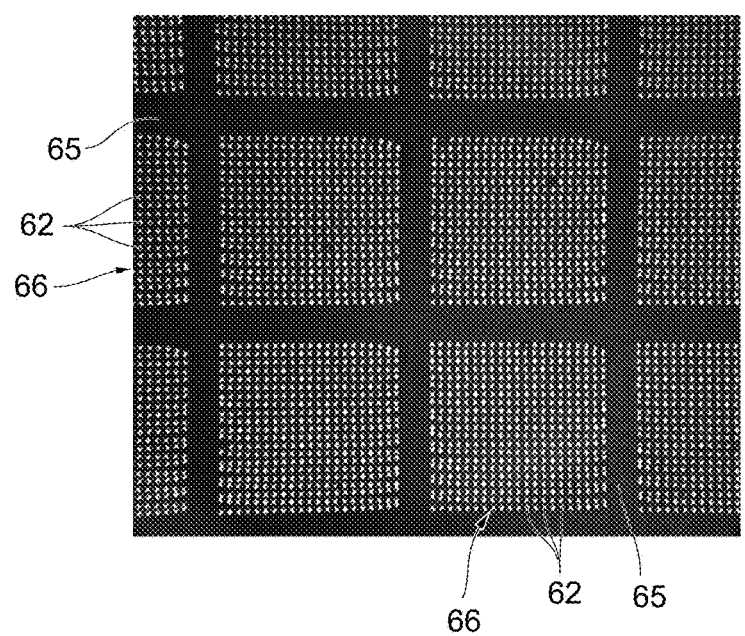
Figure 17A:
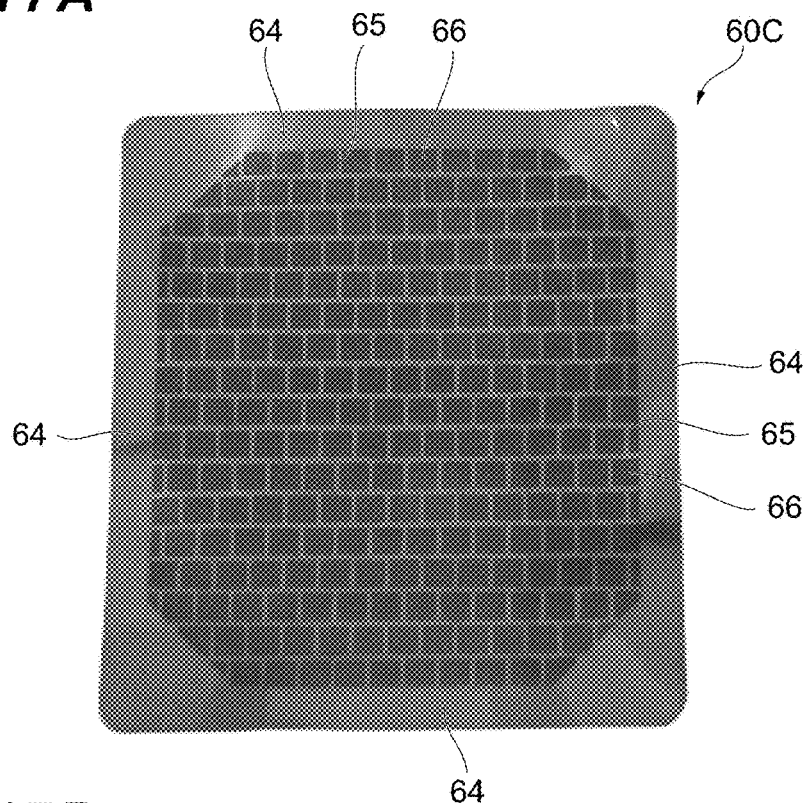
Figure 17B:
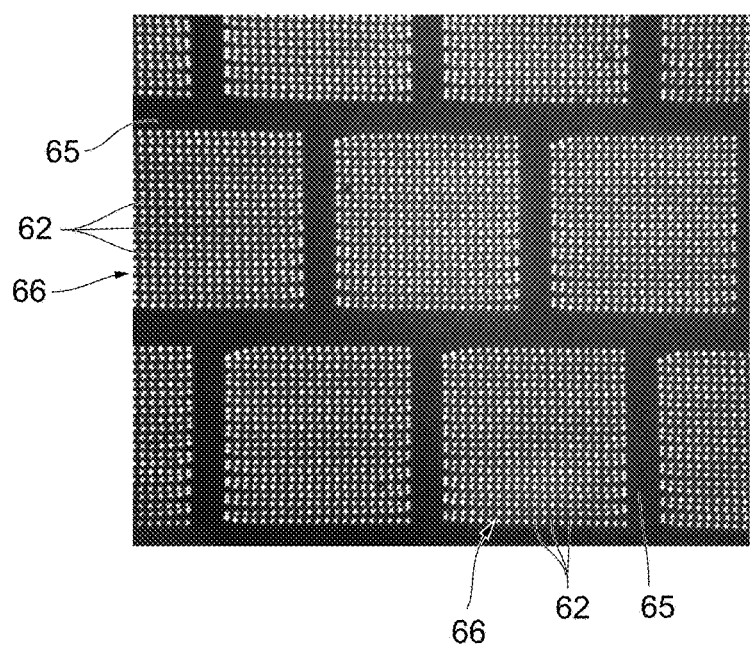

Next, FIG. 16 and FIG. 17 show other configuration examples of a porous plate in which the square pore perforation cells 66 are formed in a uniform (isotropic) distribution. Of these drawings, FIG. 16 is a sample image of a porous plate 60B in which the square pore perforation cells 66 are formed in a square lattice shape, and FIG. 16A is an external view (overall observation image) and FIG. 16B is a partially enlarged view (enlarged observation image) of the pore perforation section 63. Similarly, FIG. 17 is a sample image of a porous plate 60c in which the square pore perforation cells 66 are formed in a staggered lattice shape, and FIG. 17A is an external view and FIG. 17B is a partially enlarged view of the pore perforation section 63.

The porous plates 60B, 60C are the substrate 61 of titanium having a plate thickness of 20 μm in which the plurality of square pore perforation cells 66 having a distance between opposite sides of 1 mm and a width of the crosspieces 65 of 200 μm are formed in a uniform distribution in the pore perforation section 63. As with the already-described porous plate 60A, each pore perforation cell 66 has a large number of pores 62 perforated therein of which the center-to-center distance (perforation pitch) in the lengthwise and crosswise directions is 50 μm and the effective opening diameter is 20 μm. The effective opening diameter actually measured was approximately 20 μm±5 μm, and the width of the crosspieces actually measured was approximately 180 μm in both lengthwise and crosswise directions.

Figures 18, 19:
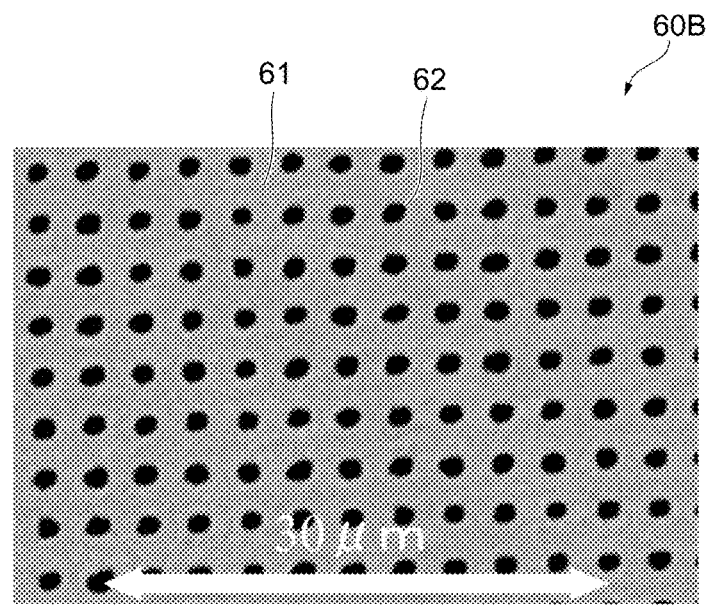
FIG. 18 is a partially enlarged view (enlarged observation image) of a porous plate for medical use, in which smaller-diameter pores are perforated in higher density, shown as yet another configuration example of the porous plate manufactured by the manufacturing method of the present invention.
FIG. 19 is a table of results of an experiment in which perforating was performed under varied conditions of a laser beam radiated to a substrate and a heat affected zone (HAZ) was examined.

FIG. 18 shows a partially enlarged observation image of a porous plate 60D as still another configuration example in which pores of a smaller diameter are perforated in higher density than in the configuration examples shown in FIG. 11 to FIG. 17. The type of material of the substrate 61 of this porous plate 60D is titanium, and the plate thickness is 20 μm. The pores 62 perforated in the substrate 61 have a pore diameter of 1 μm, and the center-to-center distance between the adjacent pores is 3 μm. It can be seen from this image that the pores 62 as small as 1 μm in pore diameter are perforated uniformly and highly densely at a small perforation pitch of 3 μm. It can also be understood that, even when the pores 62 are perforated in such high density, the substrate 61 maintains its flatness before perforating without warping or deflecting under thermal stress.

Next, FIG. 19 shows a table of results of an experiment in which perforating was performed under varied conditions of a laser beam radiated to a workpiece (the substrate of the porous plate) and the heat affected zone (HAZ; also called a heat affected layer) was examined. The conditions of the workpiece and the conditions of the pores were common, and in all the cases, the type of material was titanium (pure titanium for medical use), the plate thickness was 20 μm, and the pore diameter of the pores perforated was 15 μm. The term "heat affected zone" used in the description of this embodiment refers to a zone in which changes, such as discoloration, was found by visually observing the workpiece, in which the pores were perforated, under a microscope, and the values in the table indicate the thickness of the heat affected zone (the width of an annular changed zone) measured in the microscopic field.

Example 1 is the results of the experiment when the conditions of the laser beam radiated to the workpiece were set as follows: wavelength λ=1028 nm, average power P=300 mW, and pulse width Wp=300 fsec (femtoseconds). In this case, the thickness of the heat affected zone observed was significantly smaller than 1 μm.

Example 2 is the results of the experiment when the conditions of the laser beam radiated to the workpiece were set as follows: wavelength λ=532 nm, average power P=500 mW, and pulse width Wp=500 psec (picoseconds). In this case, the thickness of the heat affected zone observed was about 1 μm.

Example 3 is the results of the experiment when the conditions of the laser beam radiated to the workpiece were set as follows: wavelength λ=1060 nm, average power P=800 mW, and pulse width Wp=5 nse. In this case, the thickness of the heat affected zone observed was about 2 μm.

Comparative example 1 is the results of the experiment when the conditions of the laser beam radiated to the workpiece were set as follows: wavelength λ=532 nm, average power P=2 W, and pulse width Wp=40 nsec. In this case, the thickness of the heat affected zone observed was about 6 μm.

These experiment results show that the longer the pulse width of the laser beam radiated to the workpiece, the larger the thickness of the heat affected zone. These results also show that it is possible to suppress the thickness of the heat affected zone within a desired range by regulating the pulse width of the laser beam, even if the wavelength and the average power of the laser beam vary slightly. This is because, in the range of wavelength of the laser beam with which the above experiment was conducted, the absorption coefficient of the laser beam in the substrate does not vary greatly. Another reason is that the heat diffusion length does not vary according to the power of the laser beam radiated.

Figure 20:
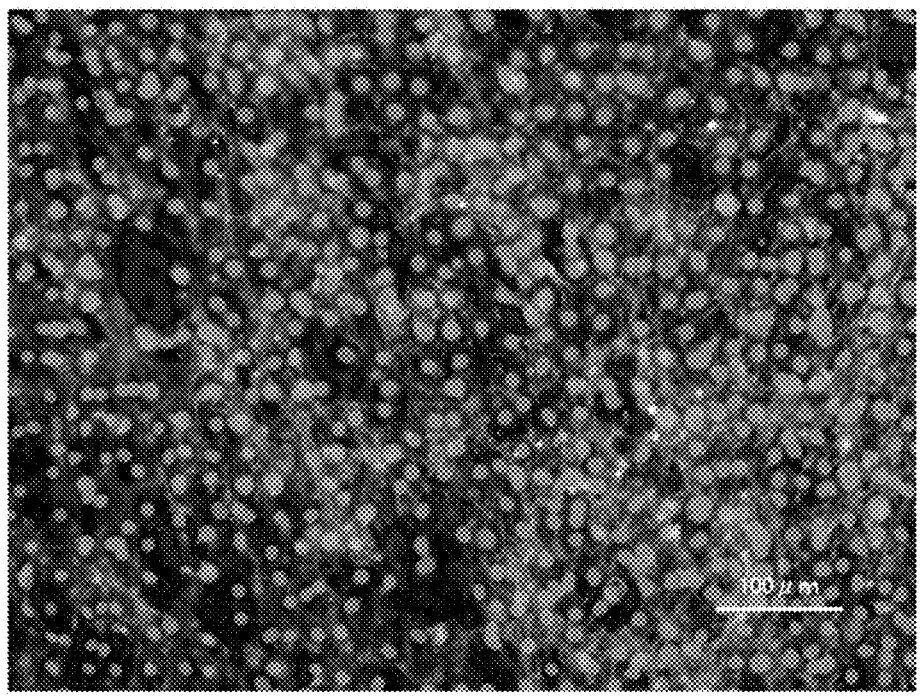
FIG. 20 is an example of results of an experiment for verifying the effect of cell adhesion to the porous plate for medical use.
Figure 21:
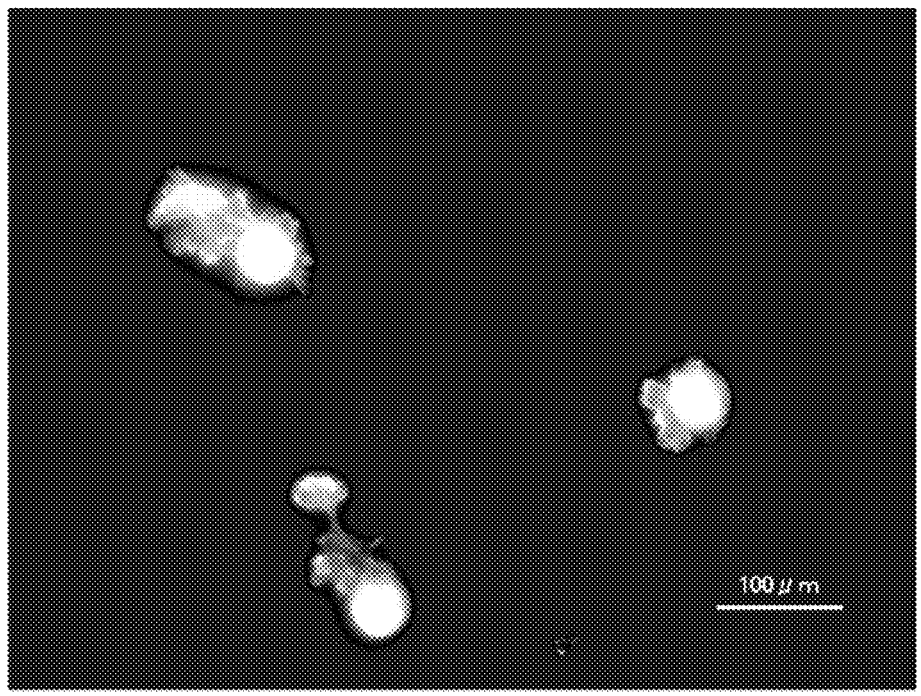
FIG. 21 is an example of results of an experiment for verifying the effect of cell adhesion to a porous plate for medical use (comparative example).

FIG. 20 and FIG. 21 are enlarged micrographs of results of an experiment on cell adhesion to a titanium porous plate. FIG. 20 shows the results of the experiment on cell adhesion to a porous plate in which the pore diameter of the pores is 20 μm and the perforation pitch is 30 μm. In the figure, adhesion of a large number of cells can be seen in the periphery of the pores which look like dark circles. By contrast, FIG. 21 is a comparative example different from the present invention, and shows the results of the experiment on cell adhesion to a porous plate in which the minimum pore diameter of the pores is 200 μm and the perforation pitch is 300 μm. In the figure, adhesion of only a few cells can be seen in part of the periphery of the pores which look like bright circles, while no adhesion of cells can be seen in the surface matrix part. Thus, it was demonstrated that the plate of the present invention had excellent cell adhesion capacity.

REFERENCE SIGNS LIST

LS Laser processing system
10 Laser device
20 Beam scanner
25 Fθ lens
30 Stage
50 Control device
60 (60A, 60B, 60C, 60D) Porous plate
61 Substrate
62 (62a to 62d) Pore
63 Pore perforation section
64 Frame section
65 Crosspiece
66 (66a to 66f) Pore perforation cell
67 Second pore
68 Third pore
70 Cell
72 Elements and components such as bioactive substances, nutrients, and gas components
W Workpiece

The invention claimed is:

1. A porous plate for medical use made of a thin-plate substrate comprising a pore perforation section having a plurality of pores perforated therein and a frame section surrounding the pore perforation section, wherein
   the thin-plate substrate is a biocompatible metal material,
   the pore perforation section has crosspieces which extend lengthwise and crosswise in continuity with the frame section and partition the pore perforation section into a plurality of parts, and a plurality of pore perforation cells each surrounded by the crosspieces, and
   the pores perforated in the pore perforation cells have a pore diameter of 1 to 50 μm, and a center-to-center distance between adjacent pores is 2 to 200 μm.

2. The porous plate for medical use according to claim 1, wherein the thickness of the thin-plate substrate of biocompatible metal material is 2 to 100 μm.

3. The porous plate for medical use according to claim 1, wherein a size of the pore perforation cell surrounded by the crosspieces is such that an inscribed circle of the cell is 0.5 to 5 mm in diameter.

4. The porous plate for medical use according to claim 1, wherein a width of the crosspieces is 0.1 to 0.5 mm.

5. The porous plate for medical use according to claim 1, wherein, in addition to the pores, second pores having a pore diameter calculated as an equivalent circular pore diameter of 80 to 220 μm are perforated in the pore perforation cells dispersedly at a center-to-center distance of 2 to 4 mm.

6. The porous plate for medical use according to claim 1, wherein the pore perforation cells surrounded by the crosspieces each have a regular polygonal shape, and the pore perforation cells are formed in a uniform distribution in the pore perforation section.

7. The porous plate for medical sue according to claim 1, wherein the pore perforation cells surrounded by the crosspieces each have a hexagonal shape with parallel opposite sides, and the pore perforation cells are formed in a honeycomb distribution in the pore perforation section.

8. A manufacturing method of a porous plate for medical use involving irradiating a thin-plate substrate with a laser beam and perforating a plurality of pores in a pore perforation section surrounded by a frame section, wherein
   the pore perforation section, except for crosspieces which extend lengthwise and crosswise in continuity with the frame section and partition the pore perforation section into a plurality of parts, is irradiated with a laser beam having a pulse width determined on the basis of a heat diffusion length in the substrate,
   pores are perforated which have a pore diameter calculated as an equivalent circular pore diameter of 1 to 50 μm and of which a center-to-center distance between adjacent pores is 2 to 200 μm, and
   a plurality of pore perforation cells, each of which is surrounded by the crosspieces and has a plurality of the pores perforated therein, are formed in the pore perforation section.

9. The manufacturing method of a porous plate for medical use according to claim 8, wherein the substrate is a biocompatible metal material having a plate thickness of 2 to 100 μm.

10. The manufacturing method of a porous plate for medical use according to claim 8, wherein the heat diffusion length is 1 μm or less.

11. The manufacturing method of a porous plate for medical use according to claim 8, wherein the pulse width is 10 nsec or less.

12. The manufacturing method of a porous plate for medical use according to claim 8, wherein a size of the pore perforation cell surrounded by the crosspieces is such that an inscribed circle of the cell is 0.5 to 5 mm in diameter.

13. The manufacturing method of a porous plate for medical use according to claim 8, wherein a width of the crosspieces is 0.1 to 0.5 mm.

14. The manufacturing method of a porous plate for medical use according to claim 8, wherein, in addition to the pores, second pores having a pore diameter calculated as an equivalent circular pore diameter of 80 to 220 μm are perforated in the pore perforation cells dispersedly at a center-to-center distance of 2 to 4 mm.

15. The manufacturing method of a porous plate for medical use according to claim 8, wherein the pore perforation cells surrounded by the crosspieces each have a regular polygonal shape, and the pore perforation cells are formed in a uniform distribution in the pore perforation section.

16. The manufacturing method of a porous plate for medical use according to claim 8, wherein the pore perforation cells surrounded by the crosspieces each have a hexagonal shape with parallel opposite sides, and the pore perforation cells are formed in a honeycomb distribution in the pore perforation section.

\* \* \* \* \*